US012427062B2

(12) United States Patent
Friedman et al.

(10) Patent No.: US 12,427,062 B2
(45) Date of Patent: Sep. 30, 2025

(54) SYSTEMS AND METHODS FOR CROSS-LINKING TREATMENTS OF AN EYE

(71) Applicant: Avedro, Inc., Waltham, MA (US)

(72) Inventors: Marc D. Friedman, Needham, MA (US); Pavel Kamaev, Lexington, MA (US); Mikhail Smirnov, North Andover, MA (US)

(73) Assignee: Avedro, Inc., Waltham, MA (US)

( * ) Notice: Subject to any disclaimer, the term of this patent is extended or adjusted under 35 U.S.C. 154(b) by 410 days.

(21) Appl. No.: 17/509,337

(22) Filed: Oct. 25, 2021

(65) Prior Publication Data

US 2022/0151830 A1 May 19, 2022

Related U.S. Application Data

(60) Continuation of application No. 16/511,500, filed on Jul. 15, 2019, now Pat. No. 11,219,553, which is a
(Continued)

(51) Int. Cl.
*A61F 9/007* (2006.01)
*A61F 9/008* (2006.01)

(52) U.S. Cl.
CPC .......... *A61F 9/0079* (2013.01); *A61F 9/007* (2013.01); *A61F 9/008* (2013.01);
(Continued)

(58) Field of Classification Search
CPC ........ A61N 5/06; A61N 5/0613; A61N 5/062; A61N 2005/0626; A61N 2005/0627;
(Continued)

(56) References Cited

U.S. PATENT DOCUMENTS

| 3,169,459 A | 2/1965 | Friedberg et al. |
| 4,034,750 A | 7/1977 | Seiderman |

(Continued)

FOREIGN PATENT DOCUMENTS

| DE | 102008046834 | 3/2010 |
| EP | 1285679 | 2/2003 |

(Continued)

OTHER PUBLICATIONS

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164.
(Continued)

*Primary Examiner* — Ahmed M Farah
(74) *Attorney, Agent, or Firm* — K&L Gates LLP

(57) ABSTRACT

A system for corneal treatment includes a light source that activates cross-linking in at least one selected region of a cornea treated with a cross-linking agent. The light source delivers photoactivating light to the at least one selected region of the cornea according to a set of parameters. The system includes a controller that receives input relating to the cross-linking agent and the set of parameters. The controller includes computer-readable storage media storing: (A) program instructions for determining cross-linking resulting from reactions involving ROS including at least peroxides, superoxides, and hydroxyl radicals, and (B) program instructions for determining cross-linking from reactions not involving oxygen. The controller executes the program instructions to output a calculated amount of cross-linking in the at least one selected region of the cornea. In response to the calculated amount of cross-linking, the light source adjusts at least one value in the set of parameters.

10 Claims, 18 Drawing Sheets

Related U.S. Application Data division of application No. 15/140,184, filed on Apr. 27, 2016, now Pat. No. 10,350,111, which is a continuation-in-part of application No. PCT/US2015/057628, filed on Oct. 27, 2015.

(60) Provisional application No. 62/069,094, filed on Oct. 27, 2014.

(52) U.S. Cl.
CPC .............. *A61F 9/00825* (2013.01); *A61F 2009/00851* (2013.01); *A61F 2009/00872* (2013.01); *A61F 2009/00893* (2013.01)

(58) Field of Classification Search
CPC ....... A61N 5/067; A61F 9/007; A61F 9/0079; A61F 9/008; A61F 9/00821; A61F 9/00823; A61F 9/00825; A61F 2009/00851; A61F 2009/00857; A61F 2009/00872; A61F 2009/00893
USPC .............. 606/4, 5; 607/88–94, 96, 100
See application file for complete search history.

(56) References Cited

U.S. PATENT DOCUMENTS

| | | | |
|---|---|---|---|
| 4,161,013 A | 7/1979 | Grodzinsky et al. |
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,098,426 A | 3/1992 | Sklar et al. |
| 5,103,005 A | 4/1992 | Gyure et al. |
| 5,171,254 A | 12/1992 | Sher |
| 5,171,318 A | 12/1992 | Gibson et al. |
| 5,281,211 A | 1/1994 | Parel et al. |
| 5,332,802 A | 7/1994 | Kelman et al. |
| 5,450,144 A | 9/1995 | Ben Nun |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,608,472 A | 3/1997 | Szirth et al. |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B2 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,237,898 B1 | 7/2007 | Hohla et al. |
| 7,270,658 B2 | 9/2007 | Woloszko et al. |
| 7,302,189 B2 | 11/2007 | Kawahata |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,871,378 B1 | 1/2011 | Chou et al. |
| 7,898,656 B2 | 3/2011 | Yun et al. |
| 7,935,058 B2 | 5/2011 | Dupps, Jr. et al. |
| 8,111,394 B1 | 2/2012 | Borysow et al. |
| 8,115,919 B2 | 2/2012 | Yun et al. |
| 8,366,689 B2 * | 2/2013 | Marshall ................. A61F 9/008 |
| | | | 604/290 |
| 8,414,911 B2 | 4/2013 | Mattson et al. |
| 8,475,437 B2 | 7/2013 | Mrochen et al. |
| 8,574,277 B2 * | 11/2013 | Muller ................. A61N 5/062 |
| | | | 606/4 |
| 8,715,273 B2 | 5/2014 | Thyzel |
| 8,870,934 B2 | 10/2014 | Muller et al. |
| 8,995,618 B2 | 3/2015 | Gertner |
| 9,005,261 B2 | 4/2015 | Brinkmann |
| 9,498,642 B2 * | 11/2016 | Muller ................. A61K 31/14 |
| 9,707,126 B2 * | 7/2017 | Friedman ............... A61P 27/10 |
| 10,350,111 B2 * | 7/2019 | Friedman ............... A61F 9/007 |
| 2001/0041856 A1 | 11/2001 | McDaniel |
| 2001/0047012 A1 | 11/2001 | Desantis, Jr. |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0042638 A1 | 4/2002 | Iezzi et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0030908 A1 | 2/2003 | Cheng et al. |
| 2003/0135122 A1 | 7/2003 | Bambot et al. |
| 2003/0175259 A1 | 9/2003 | Karageozian et al. |
| 2003/0189689 A1 | 10/2003 | Rathjen |
| 2003/0208190 A1 | 11/2003 | Roberts et al. |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2004/0254520 A1 | 12/2004 | Porteous et al. |
| 2005/0038471 A1 | 2/2005 | Chan et al. |

(56) References Cited

U.S. PATENT DOCUMENTS

| | | |
|---|---|---|
| 2005/0096515 A1 | 5/2005 | Geng |
| 2005/0149006 A1 | 7/2005 | Peyman |
| 2005/0187599 A1 | 8/2005 | Sharkey et al. |
| 2005/0271590 A1 | 12/2005 | Schwartz et al. |
| 2006/0058592 A1 | 3/2006 | Bouma et al. |
| 2006/0106371 A1 | 5/2006 | Muhlhoff et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195074 A1 | 8/2006 | Bartoli |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0028928 A1 | 2/2007 | Peyman |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0090153 A1 | 4/2007 | Naito et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203478 A1 | 8/2007 | Herekar |
| 2007/0203547 A1 | 8/2007 | Costello et al. |
| 2007/0244470 A1 | 10/2007 | Barker, Jr. et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0033408 A1 | 2/2008 | Bueler et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1* | 6/2009 | Herekar ................ A61F 9/008 607/88 |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps, Jr. et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | de Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Omberg et al. |
| 2010/0210996 A1 | 8/2010 | Peyman |
| 2010/0271593 A1 | 10/2010 | Filar |
| 2010/0286156 A1 | 11/2010 | Pinelli |
| 2010/0317588 A1 | 12/2010 | Shoseyov et al. |
| 2010/0318017 A1 | 12/2010 | Lewis et al. |
| 2011/0044902 A1 | 2/2011 | Weiner et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0125076 A1 | 5/2011 | Kraft et al. |
| 2011/0152219 A1 | 6/2011 | Stagni |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1* | 9/2011 | Muller ................ A61N 5/0625 351/215 |
| 2011/0264082 A1 | 10/2011 | Mrochen et al. |
| 2011/0282333 A1 | 11/2011 | Herekar et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0140238 A1 | 6/2012 | Horn et al. |
| 2012/0203051 A1 | 8/2012 | Brooks et al. |
| 2012/0203161 A1 | 8/2012 | Herekar |
| 2012/0209051 A1 | 8/2012 | Blumenkranz et al. |
| 2012/0215155 A1 | 8/2012 | Muller et al. |
| 2012/0283621 A1 | 11/2012 | Muller |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0245536 A1 | 9/2013 | Friedman et al. |
| 2013/0310732 A1 | 11/2013 | Foschini et al. |
| 2014/0024997 A1* | 1/2014 | Muller ................ A61F 9/0079 604/20 |
| 2014/0066835 A1 | 3/2014 | Muller et al. |
| 2014/0114232 A1 | 4/2014 | Hafezi et al. |
| 2014/0194957 A1 | 7/2014 | Rubinfeld et al. |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0343480 A1 | 11/2014 | Kamaev et al. |
| 2014/0368793 A1* | 12/2014 | Friedman ................ A61B 3/107 351/221 |
| 2015/0085252 A1 | 3/2015 | Fujimura et al. |
| 2016/0139390 A1 | 5/2016 | Bukshtab et al. |
| 2016/0175442 A1* | 6/2016 | Kamaev ................ A61K 47/12 604/20 |
| 2018/0303667 A1* | 10/2018 | Peyman ................ A61B 5/0095 |
| 2020/0085617 A1* | 3/2020 | Rajpal ................ A61F 9/0079 |
| 2020/0107953 A1* | 4/2020 | Adler ................ A61F 9/008 |
| 2021/0369108 A1* | 12/2021 | Mukherjee ................ A61F 9/007 |

FOREIGN PATENT DOCUMENTS

| | | | |
|---|---|---|---|
| EP | 1561440 | 8/2005 | |
| EP | 1790383 | 5/2007 | |
| EP | 2253321 | 11/2010 | |
| EP | 4241748 A2 * | 9/2023 | ............ A61F 9/007 |
| IT | MI2010A001236 | 5/2010 | |
| JP | 2000/262476 | 9/2000 | |
| KG | 1376 | 8/2011 | |
| RU | 2086215 | 8/1997 | |
| RU | 2098057 | 12/1997 | |
| RU | 2121825 | 11/1998 | |
| RU | 2127099 | 3/1999 | |
| RU | 2127100 | 3/1999 | |
| RU | 2309713 | 11/2007 | |
| RU | 2359716 | 6/2009 | |
| RU | 2420330 | 6/2011 | |
| RU | 2428152 | 9/2011 | |
| RU | 2456971 | 7/2012 | |
| WO | 93/16631 | 9/1993 | |
| WO | 94/03134 | 2/1994 | |
| WO | 00/74648 | 12/2000 | |
| WO | 01/58495 | 8/2001 | |
| WO | 03/061696 | 7/2003 | |
| WO | 2004/052223 | 6/2004 | |
| WO | 2005/110397 | 11/2005 | |
| WO | 2006/012947 | 2/2006 | |
| WO | 2006/128038 | 11/2006 | |
| WO | 2007/001926 | 1/2007 | |

(56) References Cited

FOREIGN PATENT DOCUMENTS

| | | |
|---|---|---|
| WO | 2007/053826 | 5/2007 |
| WO | 2007/081750 | 7/2007 |
| WO | 2007/120457 | 10/2007 |
| WO | 2007/128581 | 11/2007 |
| WO | 2007/139927 | 12/2007 |
| WO | 2007/143111 | 12/2007 |
| WO | 2008/000478 | 1/2008 |
| WO | 2008/052081 | 5/2008 |
| WO | 2008/095075 | 8/2008 |
| WO | 2009/042159 | 4/2009 |
| WO | 2009/073213 | 6/2009 |
| WO | 2009/114513 | 9/2009 |
| WO | 2009/146151 | 12/2009 |
| WO | 2010/011119 | 1/2010 |
| WO | 2010/015255 | 2/2010 |
| WO | 2010/023705 | 3/2010 |
| WO | 2010/039854 | 4/2010 |
| WO | 2010/093908 | 8/2010 |
| WO | 2011/019940 | 2/2011 |
| WO | 2011/050360 | 4/2011 |
| WO | 2011/116306 | 9/2011 |
| WO | 2012/004726 | 1/2012 |
| WO | 2012/047307 | 4/2012 |
| WO | 2012/149570 | 11/2012 |
| WO | 2012/158991 | 11/2012 |
| WO | 2012/174453 | 12/2012 |
| WO | 2013/062910 | 5/2013 |
| WO | 2013/148713 | 10/2013 |
| WO | 2013/148895 | 10/2013 |
| WO | 2013/149075 | 10/2013 |
| WO | 2014/081875 | 5/2014 |
| WO | 2014/145666 | 9/2014 |
| WO | 2014/202736 | 12/2014 |

OTHER PUBLICATIONS

Acosta A. et al., "Corneal Stroma Regeneration in Felines After Supradescemetic Keratoprothesis Implantation," Cornea, vol. 25, No. 7, pp. 830-838; Aug. 2006.
Averianova, O. S., "Nastoyaschee I buduschee kross-linkage." Mir Ofalmologii, 2010, [online] [retrieved on Feb. 13, 2014] Retrieved from the internet: http://miroft.org.ua/publications/.html.
Baier J. et al., "Singlet Oxygen Generation by UVA Light Exposure of Endogenous Photosensitizers," Biophysical Journal, vol. 91(4), pp. 1452-1459; Aug. 15, 2006.
Ballou, D. et al., "Direct Demonstration Of Superoxide Anion Production During The Oxidation Of Reduced Flavin And Of Its Catalytic Decomposition By Erythrocuprein," Biochemical And Biophysical Research Communications vol. 36, No. 6, pp. 898-904, Jul. 11, 1969.
Barbarino, S. et al., "Post-LASIK ectasia: Stabilization and Effective Management with Riboflavin / ultraviolet A-induced collagen cross-linking," Association for Research in Vision and Ophthalmology, 2006.
Berjano E., et al., "Radio-Frequency Heating of the Cornea: Theoretical Model and In Vitro Experiments," IEEE Transactions on Biomedical Engineering, vol. 49, No. 3, pp. 196-205; Mar. 2002.
Berjano E., et al., "Ring Electrode for Radio-frequency Heating of the Cornea: Modelling and in vitro Experiments," Medical & Biological Engineering & Computing, vol. 41, pp. 630-639; Jun. 2003.
Bruel, A., "Changes In Biomechanical Properties, Composition Of Collagen And Elastin, And Advanced Glycation Endproducts Of The Rat Aorta In Relation To Age," Atherosclerosis 127, Mar. 14, 1996.
Burke, JM et al., Abstract for "Retinal proliferation in response to vitreous hemoglobin or iron", Investigative Ophthalmology & Visual Science, May 1981, 20(5), pp. 582-592.
Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238.
Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008.
Chandonnet, "CO2 Laser Annular Thermokeratoplasty: A Preliminary Study," Lasers in Surgery and Medicine, vol. 12, pp. 264-273; 1992.
Chace, KV. et al., Abstract for "The role of nonenzymatic glycosylation, transition metals, and free radicals in the formation of collagen aggregates", Arch Biochem Biophys., Aug. 1, 1991, 288(2), pp. 473-480.
Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011.
Corbett M., et al., "Effect of Collagenase Inhibitors on Corneal Haze after PRK," Exp. Eye Res., vol. 72, Issue 3, pp. 253-259; Jan. 2001.
Coskenseven E. et al., "Comparative Study of Corneal Collagen Cross-linking With Riboflavin and UVA Irradiation in Patients With Keratoconus," Journal of Refractive Surgery, vol. 25, issue 4, pp. 371-376; Apr. 2009.
"DEFINITY (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011.
Ehlers W., et al., "Factors Affecting Therapeutic Concentration of Topical Aminocaproic Acid in Traumatic Hyphema," Investigative Ophthalmology & Visual Science, vol. 31, No. 11, pp. 2389-2394; Nov. 1990.
Erskine H., "Avedro Becomes Sponsor of US FDA Clinical Trials of Corneal Collagen Crosslinking," Press Release, Mar. 16, 2010 (1 page).
Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011.
Friedman, M. et al. "Advanced Corneal Cross-Linking System with Fluorescence Dosimetry", Journal of Ophthalmology, vol. 2012, Article ID 303459, dated May 7, 2012.
Frucht-Pery, et al. "Iontophoresis-gentamicin delivery into the rabbit cornea, using a hydrogel delivery probe," Jun. 20, 2003.
Gibson, Q. et al., "The Oxidation Of Reduced Flavin Mononucleotide By Molecular Oxygen," Biochem. J. (1962) 83, 368-377.
Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).
Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009.
Gravitz L., "Laser Show in the Surgical Suite: Lasers and a century-old dye could supplant needles and thread;" technology review, MIT, Mar./Apr. 2009; retrieved from http://www.technologyreview.com/biomedicine/22088/?hlid=1767, on Sep. 26, 2011.
Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009.
Hammer Arthur et al., "Corneal Biomechanical Properties at different Corneal Cross-Linking (CXL) Irradiances," IOVS, May 2014, vol. 55, No. 5, pp. 2881-2884.
Hitzenberger et al., "Birefringence Properties Of The Human Cornea Measured With Polarization Sensitive Optical Coherence Tomography," Bull. Soc. Beige Ophtalmol., 302, 153-168, 2006.
Holmstrom, B. et al., "Riboflavin As An Electron Donor In Photochemical Reactions," 1867-1871, Nov. 29, 1960.
How to Use DEFINITY: "Frequently Asked Questions;" retrieved from http://www.definityimaging.com/how-faq.html, on Sep. 26, 2011 (3 pages) (date unknown, prior to Apr. 26, 2010).
IMEX, "KXL System: Crosslinking Para Cirugia Corneal Bibliografia Cientifica," Product Literature, Nov. 23, 2010.

(56) References Cited

OTHER PUBLICATIONS

Kamaev et al., "Photochemical Kinetics Of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Ophthalmology & Visual Science, vol. 51, No. 8, pp. 3929-3934; Aug. 2010.
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., " Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al., "Pharmacological Modification of the Epithelial Permeability by Benzalkonium Chloride in UVA/Riboflavin Corneal Collagen Cross-Linking," Current Eye Research 35(8), pp. 715-721; Mar. 2010 (7 pages).
Koller, T. et al., "Complication and failure rates after corneal crosslinking," Journal Cataract and refractive surgery, vol. 35, No. 8, Aug. 2009, pp. 1358-1362.
Koller T., et al., "Therapeutische Quervernetzung der Hornhaut mittels UVA und Riboflavin: Therapeutic Cross-Linking of the Cornea Using Riboflavin/UVA," Klinische Monatsblatter fur Augenheilkunde, vol. 224, No. 9, pp. 700-706; Sep. 2007 (7 pages).
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).
Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).
Massey, V., "Activation Of Molecular Oxygen By Flavins And Flavoproteins," The Journal of Biological Chemistry vol. 269, No. 36, Issue of Sep. 9, pp. 22459-22462, 1994 (4 pages).
Marzouky, et al., "Tensioactive-mediated Transepithelial Corneal Cross-linking—First Laboratory Report, European Ophthalmic Review, 2009, 3(2), pp. 67-70.
Lee et al., "Spectrally filtered Raman / Thomson scattering using a rubidium Vapor filter", AIAA J. 40, pp. 2504-2510 (2002).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al. "Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. Vol. 2, No. 11, Oct. 18, 2011 (pp. 3109-3118).
Meek, K.M. et al. "The Cornea and Scleera", Collagen: Structure and Mechanics, Chapter 13, pp. 359-396, 2008 (38 pages).
Korean Office Action for related Korean Application No. 10-2022-7022431; action dated Sep. 22, 2022; (6 pages).
Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
Wollensak G., "Crosslinking Treatment of Progressive Keratoconus: New Hope," Current Opinion in Ophthalmology, vol. 17(4), pp. 356-360; Aug. 2006 (5 pages).
Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).
Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).
Wong, J. et al., "Post-Lasik ectasia: PRK following previous stablization and effective management with Riboflavin / ultraviolet A-induced collagen cross-linking," Association for Research in Vision and Ophthalmology, 2006 (1 page).
Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).
Yang N., Oster G. Dye-sensitized photopolymerization in the presence of reversible oxygen carriers. J. Phys. Chem. 74, 856-860 (1970) (5 pages).
Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.
Zhang, Y. et al., "Effects of Ultraviolet-A and Riboflavin on the Interaction of Collagen and Proteoglycans during Corneal Crosslinking", Journal of Biological Chemistry, vol. 286, No. 15, dated Apr. 15, 2011 (pp. 13011-13022).
Zderic V., et al., "Drug Delivery Into the Eye With the Use of Ultrasound," J. Ultrasound Med, vol. 23(10), pp. 1349-1359; Oct. 2004 (11 pages).
Zderic V., et al., "Ultrasound-enhanced Transcorneal Drug Delivery," Cornea vol. 23, No. 8, pp. 804-811; Nov. 2004 (8 pages).
International Search Report PCT/US 2016/029559, mailed Aug. 18, 2016.
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 bages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism," J. Cataract Refract. Surg., vol. 32(5), pp. 732-741; May 2006 (10 pages).
Nesterov, A. P. "Transpalpebralny Tonometr Dlya Izmereniya Vnutriglaznogo Davleniya." Feb. 2, 2006. [online] [Retrieved Dec. 17, 2012] Retrieved from the Internet: <URL: http://grpz.ru/images/publication_pdf/27.pdf>.
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
O.V. Shilenskaya et al., "Vtorichnaya katarakta posle implantatsii myagkikh IOL," [online] Aug. 21, 2008 [retrieved Mar. 4, 2013] Retrieved from the Internet: <URL:http://www.reper.ru/rus/index.php?catid=210> (4 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).
Pallikaris I., et al., "Long-term Results of Conductive Keratoplasty for low to Moderate Hyperopia," J. Cataract Refract. Surg., vol. 31(8), pp. 1520-1529; Aug. 2005 (10 pages).
Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).

(56) References Cited

OTHER PUBLICATIONS

Pinelli R., et al., "C3-Riboflavin Treatments: Where Did We Come From? Where Are We Now?" Cataract & Refractive Surgery Today Europe, Summer 2007, pp. 36-46; Jun. 2007 (10 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Roberto Pinelli et al, "Transepithelial Tensioactive Mediated CXL", Cataract & Refractive Surgery Today Europe, p. 1, URL: http://bmctoday.net/crstodayeurope/pdfs/0409_09/pdf, XP055158069.
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli et al., "Tensioactive-mediated Transepithelial Corneal Crosslinking—First Laboratory Report", 2009, European Ophthalmic Review, 3(2), pp. 67-70.
Pinelli R., "The Italian Refractive Surgery Society (SICR) results using C3-R" presented Jun. 22-23, 2007 in Italy (13 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).
Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Rocha K., et al., "Comparative Study of Riboflavin-UVA Crosslinking and "Flash-linking" Using Surface Wave Elastometry," Journal of Refractive Surgery, vol. 24 Issue 7, pp. S748-S751; Sep. 2008 (4 pages).
Rolandi et al., "Correlation of Collagen-Linked Fluorescence and Tendon Fiber Breaking Time." Gerontology 1991;27:240-243 (4 pages).
RxList: "Definity Drug Description;" The Internet Drug Index, revised Jun. 16, 2008, retrieved from http://www.rxlist.com/definity-drug.htm, on Sep. 26, 2011 (4 pages).
Saleh et al. "Fundamentals of Photonics" 1991, pp. 74-77.
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Shell, J., "Pharmacokinetics of Topically Applied Ophthalmic Drugs," Survey of Ophthalmology, vol. 26, No. 4, pp. 207-218; Jan.-Feb. 1982 (12 pages).
Sobol E N et al, "Correction of Eye Refraction By Nonablative Laser Action On Thermomechanical Properties of Cornea and Sclera", Quantum Electronics, Turpion Ltd., London, GB, (Oct. 2002), vol. 32, No. 10, ISSN 1063-7818, pp. 909-912, XP001170947 [A] 1.

Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).
Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).
Spoerl E., et al., "Artificial Stiffening of the Cornea by Induction of Intrastromal Cross-links," Der Ophthalmologe, vol. 94, No. 12, pp. 902-906; Dec. 1997 (5 pages).
Spoerl E., et al., "Induction of Cross-links in Corneal Tissue," Experimental Eye Research, vol. 66, Issue 1, pp. 97-103; Jan. 1998 (7 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Techniques for Stiffening the Cornea," Journal of Refractive Surgery, vol. 15, Issue 6, pp. 711-713; Nov.-Dec. 1999 (4 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
"Tahzib N.G. et al., ""Recurrent intraocular inflamation after implantation of the Artiflex phakic intraocular lens for the correction of high myopia,"" J Cataract Refract Surg, Aug. 2006; 32(8)1388-91, (abstract) [online] [Retrived Mar. 4, 2013] Retrieved from PubMed, PMID: 16863981".
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thornton, I. et al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.
Thornton et al (Investigative Ophthalmology and Visual Science, Mar. 2009, vol. 50, No. 3, pp. 1227-1233).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Tomlinson et al. (Investigative Opthalmology and Visual Science 2006, 47 (10), 4309, 4315.
Trembly et al., "Microwave Thermal Keratoplasty for Myopia: Keratoscopic Evaluation in Porcine Eyes," Journal of Refractive Surgery, vol. 17, No. 6, pp. 682-688; Nov./Dec. 2001 (8 pages).
Turgunbaev N.A. et al. Fotomodifikatsiya sklery u bolnykh s progressiruyuschei blizorukostyu (predvaritelnoe soobschenie). 2010 [online]. Retrieved from the Internet:<URL: http://www.eyepress.ru/article.aspx?7484> (2 pages).
"UV-X: Radiation System for Treatment of Keratokonus," PESCHKE Meditrade GmbH; retrieved from http://www.peschkemed.ch/ on Sep. 27, 2011 (date unknown, prior to Sep. 16, 2008) (1 page).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).

\* cited by examiner

Upper 100 um of flap

Flap slice from 100 to 200 um

| Protocol | Reporting source | Measured depth (μm) | Calculated depth (μm) |
|---|---|---|---|
| 30 min presoak (for calculations) 3 mW/cm², 30 min treatment (Dresden) (5.4 J/cm²) | [1] [2] [3] | 291.4±2.9 350 350.97 ± 31.94 μm (range, 280-361 μm) centrally, and 210.4±31.91 μm (range, 150-261 μm) temporally 350.78 μm ±40.34 (SD) (range 256.6 to 449.0 μm) | 290 |
| 15 min presoak 30 mW/cm², 3 min treatment (Accelerated, 5.4 J/cm²) | [4] | 140.4±39.1 | 120 |
| 15 min presoak 30 mW/cm², 4 min treatment (7.2 J/cm²) | [4] | 153.65±33.11 | 143 |
| 10 min presoak 15 mW/cm² (average), 8 min treatment (7.2 J/cm²) 1 sec on and 1 sec off | [4] | 213±47 | 202 |
| 10 min presoak 10 mW/cm² (average), 12 min treatment (7.2 J/cm²) 2 sec on and 1 sec off | [4] | 233±92 | 245 |
| 15 min presoak 12 mW/cm² (average), 10 min treatment (7.2 J/cm²) | [5,6] | 150-200 | 223 |
| 20 min presoak 30 mW/cm² (average), 4 min treatment (7.2 J/cm²) | [5,6] | 140-180 | 143 |
| 10 minutes with 9 mW/cm² of UVA (5.4 J/cm²) | [7] | 288.46 ± 42.37 μm (range 238.5 to 363.5 μm) | 200 |

FIG. 6B

1. Yam JC, et al., Corneal collagen cross-linking demarcation line depth assessed by Visante OCT after CXL for keratoconus and corneal ectasia. J Refract Surg. (Jul. 2012), 28(7):475-81.
2. Kymionis GD, et al., Corneal stroma demarcation line after standard and high-intensity collagen crosslinking determined with anterior segment optical coherence tomography, J Cataract Refract Surg. (May 2014), 40(5):736-40.
3. Theo Seiler, MD, PhD and Farhad Hafezi, MD., Corneal Cross-Linking-Induced Stromal Demarcation line, Cornea (2006), 25:1057--1059.
4. Luigi Fontana and Antonello Moramarco. Esperienze personali con CXL accelerato, UOC Oculistica ASMN-IRCCS Reggio Emilia. Roma, 20 Sept. 2014.
5. C. Mazzotta. In Vivo Corneal Micro-Structural Analysis in Accelerated Corneal Collagen X-Linking. UOC Oculistica ASMN-IRCCS Reggio Emilia. Roma, 20 Sept. 2014.
6. Cosimo Mazzotta. et al., Qualitative Investigation of Corneal Changes after Accelerated Corneal Collagen Cross-linking (A-CXL) by In vivo Confocal Microscopy and Corneal OCT, J Clin Exp Ophthalmol (2013), 4:6.
7. George D Kymionis, et al., Evaluation of the corneal collagen cross-linking demarcation line profile using anterior segment optical coherence tomography, Cornea (2013), 32: 907-10.

SYSTEMS AND METHODS FOR CROSS-LINKING TREATMENTS OF AN EYE

CROSS REFERENCE TO RELATED APPLICATIONS

This application is a continuation application of U.S. patent application Ser. No. 16/511,500, filed Jul. 15, 2019, which is a divisional application of U.S. patent application Ser. No. 15/140,184, filed on Apr. 27, 2016, which is a continuation-in-part application of PCT Application No. PCT/US2015/057628, filed on Oct. 27, 2015, which claims priority to U.S. Provisional Patent Application No. 62/069,094, filed Oct. 27, 2014, the contents of these applications being incorporated entirely herein by reference.

BACKGROUND OF THE INVENTION

Field of the Invention

The present disclosure pertains to systems and methods for treating disorders of the eye, and more particularly, to systems and methods for cross-linking treatments of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

BRIEF DESCRIPTION OF THE DRAWINGS

FIGS. 6A-B illustrate graphs showing the correlation between model values and experimental data for corneal stromal demarcation line experiments, where the model values are based on a model of photochemical kinetic reactions according to aspects of the present disclosure.

SUMMARY

Figure 1:
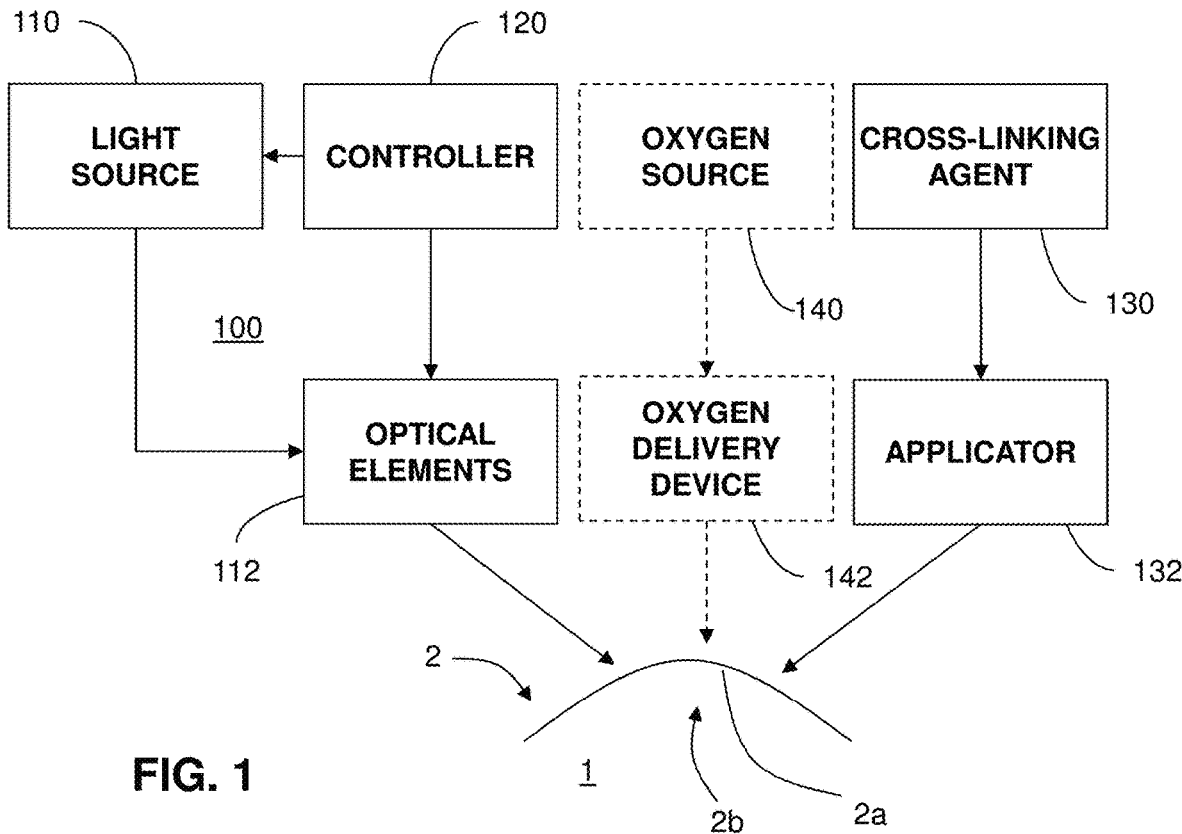
FIG. 1 illustrates an example system that delivers a cross-linking agent and photoactivating light to a cornea of an eye in order to generate cross-linking of corneal collagen, according to aspects of the present disclosure.

According to aspects of the present disclosure, an example system for corneal treatment includes a light source configured to activate cross-linking in at least one selected region of a cornea treated with a cross-linking agent. The light source is configured to deliver photoactivating light to the at least one selected region of the cornea according to a set of parameters. The system also includes a controller configured to receive input relating to the cross-linking agent and the set of parameters for the delivery of the photoactivating light. The controller includes computer-readable storage media storing: (A) a first set of program instructions for determining, from the input, cross-linking resulting from reactions involving reactive oxygen species (ROS) including at least peroxides, superoxides, and hydroxyl radicals, and (B) a second set of program instructions for determining, from the input, cross-linking from reactions not involving oxygen. The controller is configured to execute the first and second sets of program instructions to output a calculated amount of cross-linking in the at least one selected region of the cornea. In response to the calculated amount of cross-linking output by the controller, the light source is configured to adjust at least one value in the set of parameters for the delivery of the photoactivating light.

According to further aspects of the present disclosure, an example system for conical treatment includes a light source configured to activate cross-linking in at least one selected region of a cornea treated with a cross-linking agent. The light source is configured to deliver photoactivating light to the at least one selected region of the cornea according to a set of parameters. The system also includes an oxygen source and an oxygen delivery device configured to provide a concentration of oxygen from the oxygen source to the at least one selected region of the cornea. The system also includes a controller configured to receive input relating to the cross-linking agent, the set of parameters for the delivery of the photoactivating light, and the concentration of oxygen. The controller includes computer-readable storage media storing: (A) a first set of program instructions for determining, from the input, cross-linking resulting from reactions involving reactive oxygen species (ROS) including at least peroxides, superoxides, and hydroxyl radicals, and (B) a second set of program instructions for determining, from the input, cross-linking from reactions not involving oxygen. The controller is configured to execute the first and second sets of program instructions to output a calculated amount of cross-linking in the at least one selected region of the cornea, the calculated amount of cross-linking indicating a three-dimensional distribution of cross-links. In response to the calculated amount of the cross-linking activity output by the controller, at least one of: (i) the light source is configured to adjust at least one value in the set of parameters for the delivery of the photoactivating light, or (ii) the oxygen delivery device is configured to adjust a value of the concentration of oxygen delivered to the at least one selected region of the cornea.

According to yet further aspects of the present disclosure, an example system for corneal treatment includes an illumination system configured to deliver photoactivating light to a cross-linking agent applied to a cornea. The photoactivating light generates cross-linking activity with the cross-linking agent. The system also includes a controller including one or more processors and computer-readable storage media. The controller is configured to receive input relating to a desired biomechanical change in the cornea and to execute, with the one or more processors, program instructions stored on the storage media to determine, from a photochemical kinetic model, a three-dimensional distribution of cross-links for the cornea to achieve the desired biomechanical change in the cornea. The photochemical kinetic model calculates the distribution of cross-links based on cross-linking from (A) reactions involving reactive oxygen species (ROS) including at least peroxides, superoxides, and hydroxyl radicals, and (B) reactions not involving oxygen. The controller is configured to execute the program instructions also to determine at least one set of treatment parameters to achieve the distribution of cross-links. The at least one set of treatment parameters includes illumination parameters for the delivery of the photoactivating light by the illumination system. In response to the determination of the at least one set of treatment parameters, the illumination system is configured to deliver the photoactivating light to the cornea according to the illumination parameters.

In some embodiments, the controller may be configured to execute the program instructions to determine a plurality of sets of treatment parameters to achieve the distribution of cross-links. The illumination system is configured to deliver the photoactivating light according to the illumination parameters in a selected one of the sets of treatment parameters.

In further embodiments, the controller may be configured to receive information relating to one or more preferences for the treatment parameters and to execute further program instructions to determine the selected set of treatment parameters according to the one or more preferences.

DESCRIPTION

FIG. 1 illustrates an example treatment system 100 for generating cross-linking of collagen in a cornea 2 of an eye 1. The treatment system 100 includes an applicator 132 for applying a cross-linking agent 130 to the cornea 2. In example embodiments, the applicator 132 may be an eye dropper, syringe, or the like that applies the photosensitizer 130 as drops to the cornea 2. The cross-linking agent 130 may be provided in a formulation that allows the cross-linking agent 130 to pass through the corneal epithelium 2a and to underlying regions in the corneal stroma 2b. Alternatively, the corneal epithelium 2a may be removed or otherwise incised to allow the cross-linking agent 130 to be applied more directly to the underlying tissue.

The treatment system 100 includes an illumination system with a light source 110 and optical elements 112 for directing light to the cornea 2. The light causes photoactivation of the cross-linking agent 130 to generate cross-linking activity in the cornea 2. For example, the cross-linking agent may include riboflavin and the photoactivating light may be ultraviolet A (UVA) (e.g., 365 nm) light. Alternatively, the photoactivating light may have another wavelength, such as a visible wavelength (e.g., 452 nm). As described further below, corneal cross-linking improves corneal strength by creating chemical bonds within the corneal tissue according to a system of photochemical kinetic reactions. For instance, riboflavin and the photoactivating light are applied to stabilize and/or strengthen corneal tissue to address diseases such as keratoconus or post-LASIK ectasia.

The treatment system 100 includes one or more controllers 120 that control aspects of the system 100, including the light source 110 and/or the optical elements 112. In an implementation, the cornea 2 can be more broadly treated with the cross-linking agent 130 (e.g., with an eye dropper, syringe, etc.), and the photoactivating light from the light source 110 can be selectively directed to regions of the treated cornea 2 according to a particular pattern.

The optical elements 112 may include one or more mirrors or lenses for directing and focusing the photoactivating light emitted by the light source 110 to a particular pattern on the cornea 2. The optical elements 112 may further include filters for partially blocking wavelengths of light emitted by the light source 110 and for selecting particular wavelengths of light to be directed to the cornea 2 for activating the cross-linking agent 130. In addition, the optical elements 112 may include one or more beam splitters for dividing a beam of light emitted by the light source 110, and may include one or more heat sinks for absorbing light emitted by the light source 110. The optical elements 112 may also accurately and precisely focus the photo-activating light to particular focal planes within the cornea 2, e.g., at a particular depths in the underlying region 2b where cross-linking activity is desired.

Moreover, specific regimes of the photoactivating light can be modulated to achieve a desired degree of cross-linking in the selected regions of the cornea 2. The one or more controllers 120 may be used to control the operation of the light source 110 and/or the optical elements 112 to precisely deliver the photoactivating light according to any combination of: wavelength, bandwidth, intensity, power, location, depth of penetration, and/or duration of treatment (the duration of the exposure cycle, the dark cycle, and the ratio of the exposure cycle to the dark cycle duration).

The parameters for photoactivation of the cross-linking agent 130 can be adjusted, for example, to reduce the amount of time required to achieve the desired cross-linking. In an example implementation, the time can be reduced from minutes to seconds. While some configurations may apply the photoactivating light at an irradiance of 5 mW/cm$^2$, larger irradiance of the photoactivating light, e.g., multiples of 5 mW/cm$^2$, can be applied to reduce the time required to achieve the desired cross-linking. The total dose of energy absorbed in the cornea 2 can be described as an effective dose, which is an amount of energy absorbed through an area of the corneal epithelium 2a. For example the effective dose for a region of the corneal surface 2A can be, for example, 5 J/cm$^2$, or as high as 20 J/cm$^2$ or 30 J/cm$^2$. The effective dose described can be delivered from a single application of energy, or from repeated applications of energy.

The optical elements 112 of the treatment system 100 may include a digital micro-mirror device (DMD) to modulate the application of photoactivating light spatially and temporally. Using DMD technology, the photoactivating light from the light source 110 is projected in a precise spatial pattern that is created by microscopically small mirrors laid out in a matrix on a semiconductor chip. Each mirror represents one or more pixels in the pattern of projected light. With the DMD one can perform topography guided cross-linking. The control of the DMD according to topography may employ several different spatial and temporal irradiance and dose profiles. These spatial and temporal dose profiles may be created using continuous wave illumination but may also be modulated via pulsed illumination by pulsing the illumination source under varying frequency and duty cycle regimes as described above. Alternatively, the DMD can modulate different frequencies and duty cycles on a pixel by pixel basis to give ultimate flexibility using continuous wave illumination. Or alternatively, both pulsed illumination and modulated DMD frequency and duty cycle combinations may be combined. This allows for specific amounts of spatially determined corneal cross-linking. This spatially determined cross-linking may be combined with dosimetry, interferometry, optical coherence tomography (OCT), corneal topography, etc., for pre-treatment planning and/or real-time monitoring and modulation of corneal cross-linking during treatment. Additionally, pre-clinical patient information may be combined with finite element biomechanical computer modeling to create patient specific pre-treatment plans.

To control aspects of the delivery of the photoactivating light, embodiments may also employ aspects of multiphoton excitation microscopy. In particular, rather than delivering a single photon of a particular wavelength to the cornea 2, the treatment system 100 may deliver multiple photons of longer wavelengths, i.e., lower energy, that combine to initiate the cross-linking. Advantageously, longer wavelengths are scattered within the cornea 2 to a lesser degree than shorter wavelengths, which allows longer wavelengths of light to penetrate the cornea 2 more efficiently than shorter wavelength light. Shielding effects of incident irradiation at deeper depths within the cornea are also reduced over conventional short wavelength illumination since the absorption of the light by the photosensitizer is much less at the longer wavelengths. This allows for enhanced control over depth specific cross-linking. For example, in some embodiments, two photons may be employed, where each photon carries approximately half the energy necessary to excite the molecules in the cross-linking agent 130 to generate the photochemical kinetic reactions described further below. When a cross-linking agent molecule simultaneously absorbs both photons, it absorbs enough energy to release reactive radicals in the corneal tissue. Embodiments may also utilize lower energy photons such that a cross-linking agent molecule must simultaneously absorb, for example, three, four, or five, photons to release a reactive radical. The probability of the near-simultaneous absorption of multiple photons is low, so a high flux of excitation photons may be required, and the high flux may be delivered through a femtosecond laser.

A large number of conditions and parameters affect the cross-linking of corneal collagen with the cross-linking agent 130. For example, when the cross-linking agent 130 is riboflavin and the photoactivating light is UVA light, the irradiance and the dose both affect the amount and the rate of cross-linking. The UVA light may be applied continuously (continuous wave (CW)) or as pulsed light, and this selection has an effect on the amount, the rate, and the extent of cross-linking.

If the UVA light is applied as pulsed light, the duration of the exposure cycle, the dark cycle, and the ratio of the exposure cycle to the dark cycle duration have an effect on the resulting corneal stiffening. Pulsed light illumination can be used to create greater or lesser stiffening of corneal tissue than may be achieved with continuous wave illumination for the same amount or dose of energy delivered. Light pulses of suitable length and frequency may be used to achieve more optimal chemical amplification. For pulsed light treatment, the on/off duty cycle may be between approximately 1000/1 to approximately 1/1000; the irradiance may be between approximately 1 mW/cm$^2$ to approximately 1000 mW/cm$^2$ average irradiance, and the pulse rate may be between approximately 0.01 HZ to approximately 1000 Hz or between approximately 1000 Hz to approximately 100,000 Hz.

The treatment system 100 may generate pulsed light by employing a DMD, electronically turning the light source 110 on and off, and/or using a mechanical or opto-electronic (e.g., Pockels cells) shutter or mechanical chopper or rotating aperture. Because of the pixel specific modulation capabilities of the DMD and the subsequent stiffness impartment based on the modulated frequency, duty cycle, irradiance and dose delivered to the cornea, complex biomechanical stiffness patterns may be imparted to the cornea to allow for various amounts of refractive correction. These refractive corrections, for example, may involve combinations of myopia, hyperopia, astigmatism, irregular astigmatism, presbyopia and complex corneal refractive surface corrections because of ophthalmic conditions such as keratoconus, pellucid marginal disease, post-lasik ectasia, and other conditions of corneal biomechanical alteration/degeneration, etc. A specific advantage of the DMD system and method is that it allows for randomized asynchronous pulsed topographic patterning, creating a non-periodic and uniformly appearing illumination which eliminates the possibility for triggering photosensitive epileptic seizures or flicker vertigo for pulsed frequencies between 2 Hz and 84 Hz.

Although example embodiments may employ stepwise on/off pulsed light functions, it is understood that other functions for applying light to the cornea may be employed to achieve similar effects. For example, light may be applied to the cornea according to a sinusoidal function, sawtooth function, or other complex functions or curves, or any combination of functions or curves. Indeed, it is understood that the function may be substantially stepwise where there may be more gradual transitions between on/off values. In addition, it is understood that irradiance does not have to decrease down to a value of zero during the off cycle, and may be above zero during the off cycle. Desired effects may be achieved by applying light to the cornea according to a curve varying irradiance between two or more values.

Examples of systems and methods for delivering photoactivating light are described, for example, in U.S. Patent Application Publication No. 2011/0237999, filed Mar. 18, 2011 and titled "Systems and Methods for Applying and Monitoring Eye Therapy," U.S. Patent Application Publication No. 2012/0215155, filed Apr. 3, 2012 and titled "Systems and Methods for Applying and Monitoring Eye Therapy," and U.S. Patent Application Publication No. 2013/0245536, filed Mar. 15, 2013 and titled "Systems and Methods for Corneal Cross-Linking with Pulsed Light," the contents of these applications being incorporated entirely herein by reference.

The addition of oxygen also affects the amount of corneal stiffening. In human tissue, $O_2$ content is very low compared to the atmosphere. The rate of cross-linking in the cornea, however, is related to the concentration of $O_2$ when it is irradiated with photoactivating light. Therefore, it may be advantageous to increase or decrease the concentration of $O_2$ actively during irradiation to control the rate of cross-linking until a desired amount of cross-linking is achieved. Oxygen may be applied during the cross-linking treatments in a number of different ways. One approach involves supersaturating the riboflavin with $O_2$. Thus, when the riboflavin is applied to the eye, a higher concentration of $O_2$ is delivered directly into the cornea with the riboflavin and affects the reactions involving $O_2$ when the riboflavin is exposed to the photoactivating light. According to another approach, a steady state of $O_2$ (at a selected concentration) may be maintained at the surface of the cornea to expose the cornea to a selected amount of $O_2$ and cause $O_2$ to enter the cornea. As shown in FIG. 1, for instance, the treatment system 100 also includes an oxygen source 140 and an oxygen delivery device 142 that optionally delivers oxygen at a selected concentration to the cornea 2. Example systems and methods for applying oxygen during cross-linking treatments are described, for example, in U.S. Pat. No. 8,574,277, filed Oct. 21, 2010 and titled "Eye Therapy," U.S. Patent Application Publication No. 2013/0060187, filed Oct. 31, 2012 and titled "Systems and Methods for Corneal Cross-Linking with Pulsed Light," the contents of these applications being incorporated entirely herein by reference.

When riboflavin absorbs radiant energy, especially light, it undergoes photo activation. There are two photochemical kinetic pathways for riboflavin photoactivation, Type I and Type II. Some of the reactions involved in both the Type I and Type II mechanisms are as follows:

Common Reactions:

$$Rf \rightarrow Rf_1^*, I; \qquad (r1)$$

$$Rf_1^* \rightarrow Rf, \kappa 1; \qquad (r2)$$

$$Rf_1^* \rightarrow Rf_3^*, \kappa 2; \qquad (r3)$$

Type I Reactions:

$$Rf_3^* + DH \rightarrow RfH^- + D^-, \kappa 3; \qquad (r4)$$

$$2RfH^- \rightarrow Rf + RfH_2, \kappa 4; \qquad (r5)$$

Type II Reactions:

$$Rf_3^* + O_2 \rightarrow Rf + O_2^1, \kappa 5; \qquad (r6)$$

$$DH + O_2^1 \rightarrow D_{ox}, \kappa 6; \qquad (r7)$$

$$D_{ox} + DH \rightarrow D - D, \kappa 7; CXL \qquad (r8)$$

In the reactions described herein, Rf represents riboflavin in the ground state. $Rf_1^*$ represents riboflavin in the excited singlet state. $Rf_3^*$ represents riboflavin in a triplet excited state. $Rf^{*-}$ is the reduced radical anion form of riboflavin. $RfH^*$ is the radical form of riboflavin. $RfH_2$ is the reduced form of riboflavin. DH is the substrate. $DH^{*+}$ is the intermediate radical cation. $D^*$ is the radical. $D_{ox}$ is the oxidized form of the substrate.

Riboflavin is excited into its triplet excited state $Rf_3^*$ as shown in reactions (r1) to (r3). From the triplet excited state $Rf_3^*$, the riboflavin reacts further, generally according to Type I or Type II mechanisms. In the Type I mechanism, the substrate reacts with the excited state riboflavin to generate radicals or radical ions, respectively, by hydrogen atoms or electron transfer. In Type II mechanism, the excited state riboflavin reacts with oxygen to form singlet molecular oxygen. The singlet molecular oxygen then acts on tissue to produce additional cross-linked bonds.

Oxygen concentration in the cornea is modulated by UVA irradiance and temperature and quickly decreases at the beginning of UVA exposure. Utilizing pulsed light of a specific duty cycle, frequency, and irradiance, input from both Type I and Type II photochemical kinetic mechanisms can be employed to achieve a greater amount of photochemical efficiency. Moreover, utilizing pulsed light allows regulating the rate of reactions involving riboflavin. The rate of reactions may either be increased or decreased, as needed, by regulating, one of the parameters such as the irradiance, the dose, the on/off duty cycle, riboflavin concentration, soak time, and others. Moreover, additional ingredients that affect the reaction and cross-linking rates may be added to the cornea.

If UVA radiation is stopped shortly after oxygen depletion, oxygen concentrations start to increase (replenish). Excess oxygen may be detrimental in the corneal cross-linking process because oxygen is able to inhibit free radical photopolymerization reactions by interacting with radical species to form chain-terminating peroxide molecules. The pulse rate, irradiance, dose, and other parameters can be adjusted to achieve a more optimal oxygen regeneration rate. Calculating and adjusting the oxygen regeneration rate is another example of adjusting the reaction parameters to achieve a desired amount of corneal stiffening.

Oxygen content may be depleted throughout the cornea, by various chemical reactions, except for the very thin corneal layer where oxygen diffusion is able to keep up with the kinetics of the reactions. This diffusion-controlled zone will gradually move deeper into the cornea as the reaction ability of the substrate to uptake oxygen decreases.

Riboflavin is reduced (deactivated) reversibly or irreversibly and/or photo-degraded to a greater extent as irradiance increases. Photon optimization can be achieved by allowing reduced riboflavin to return to ground state riboflavin in Type I reactions. The rate of return of reduced riboflavin to ground state in Type I reactions is determined by a number of factors. These factors include, but are not limited to, on/off duty cycle of pulsed light treatment, pulse rate frequency, irradiance, and dose. Moreover, the riboflavin concentration, soak time, and addition of other agents, including oxidizers, affect the rate of oxygen uptake. These and other parameters, including duty cycle, pulse rate frequency, irradiance, and dose can be selected to achieve more optimal photon efficiency and make efficient use of both Type I as well as Type II photochemical kinetic mechanisms for riboflavin photosensitization. Moreover, these parameters can be selected in such a way as to achieve a more optimal chemical amplification effect.

In addition to the photochemical kinetic reactions (r1)-(r8) above, however, the present inventors have identified the following photochemical kinetic reactions (r9)-(r26) that also occur during riboflavin photoactivation:

$$Rf_3^* \rightarrow Rf, \kappa8; \quad (r9)$$

$$Rf_3^* + Rf \rightarrow 2RfH^\cdot, \kappa9; \quad (r10)$$

$$RfH_2 + O_2 \rightarrow RfH^\cdot + H^+ + O_2^-, \kappa10; \quad (r11)$$

$$RfH^\cdot + O_2 \rightarrow Rf + H^+ + O_2^-, \kappa11; \quad (r12)$$

$$2RfH_2 + O_2^- \rightarrow 2RfH^\cdot + H_2O_2, \kappa12; \quad (r13)$$

$$2RfH^\cdot + O_2^- \rightarrow 2Rf + H_2O_2, \kappa13; \quad (r14)$$

$$RfH^\cdot + H_2O_2 \rightarrow OH^\cdot + Rf + H_2O, \kappa14; \quad (r15)$$

$$OH^\cdot + DH \rightarrow D^\cdot + H_2O, \kappa15; \quad (r16)$$

$$D^\cdot + D^\cdot \rightarrow D-D, \kappa16; \quad CXL \quad (r17)$$

$$O_2^1 \rightarrow O_2, \kappa18; \quad (r18)$$

$$D^\cdot + RfH_2 \rightarrow RfH^\cdot + DH, \kappa19; \quad (r19)$$

$$Rf + Rf \underset{\kappa_a^-}{\overset{\kappa_a^+}{\rightleftarrows}} A_1, \kappa_a = \kappa_a^+/\kappa_a^- \quad (r20)$$

$$RfH_2 + RfH_2 \underset{\kappa_a^-}{\overset{\kappa_a^+}{\rightleftarrows}} A_2, \kappa_a = \kappa_a^+/\kappa_a^- \quad (r21)$$

$$Rf + RfH_2 \underset{\kappa_b^-}{\overset{\kappa_b^+}{\rightleftarrows}} A_3, \kappa_b = \kappa_b^+/\kappa_b^- \quad (r22)$$

$$Rf_1^* + A \rightarrow Rf + A, \kappa_{1a} \quad (r23)$$

$$Rf_3^* + A \rightarrow Rf + A, \kappa_{3a} \quad (r24)$$

$$2O_2^- \rightarrow O_2 + H_2O_2, \kappa12 \quad (r25)$$

$$OH^\circ + CXL \rightarrow \text{inert products}, \kappa_{OH} \quad (r26)$$

Figure 2A:
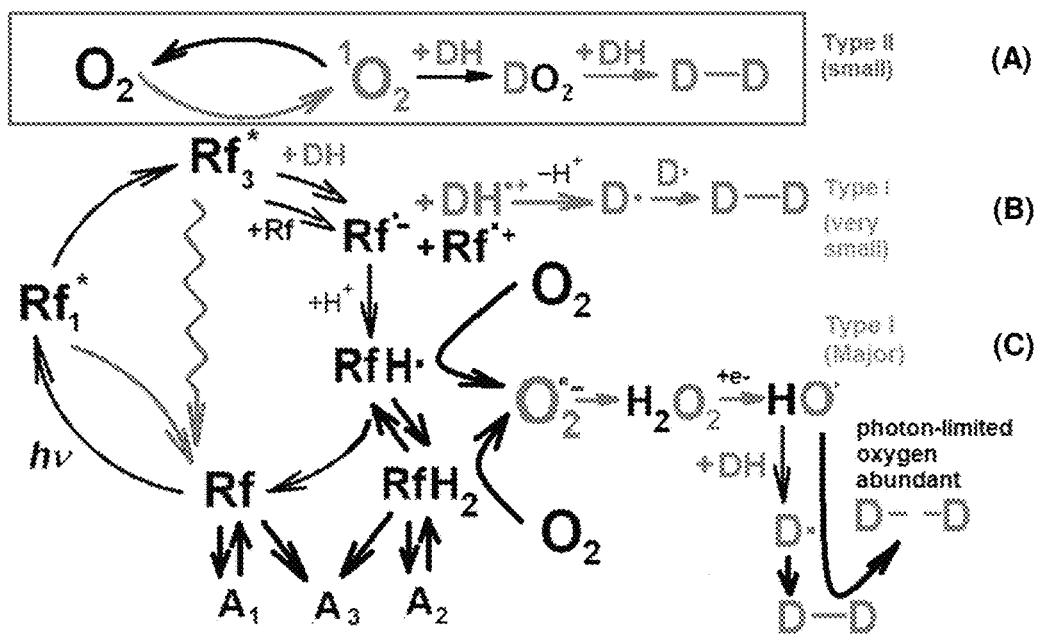
FIGS. 2A-B illustrate a diagram for photochemical kinetic reactions involving riboflavin and photoactivating light (e.g., ultraviolet A (UVA) light) applied during a corneal cross-linking treatment, according to aspects of the present disclosure.

FIG. 2A illustrates a diagram for the photochemical kinetic reactions provided in reactions (r1) through (r26) above. The diagram summarizes photochemical transformations of riboflavin (Rf) under UVA photoactivating light and its interactions with various donors (DH) via electron transfer. As shown, cross-linking activity occurs: (A) through the presence of singlet oxygen in reactions (r6) through (r8) (Type II mechanism); (B) without using oxygen in reactions (r4) and (r17) (Type I mechanism); and (C) through the presence of peroxide ($H_2O_2$), superoxide ($O_2^-$), and hydroxyl radicals ($^-OH$) in reactions (r13) through (r17).

As shown in FIG. 2A, the present inventors have also determined that the cross-linking activity is generated to a greater degree from reactions involving peroxide, superoxide, and hydroxyl radicals. Cross-linking activity is generated to a lesser degree from reactions involving singlet oxygen and from non-oxygen reactions. Some models based on the reactions (r1)-(r26) may account for the level of cross-linking activity generated by the respective reactions. For instance, where singlet oxygen plays a smaller role in generating cross-linking activity, models may be simplified by treating the cross-linking activity resulting from singlet oxygen as a constant.

All the reactions start from $Rf_3^*$ as provided in reactions (r1)-(r3). The quenching of $Rf_3^*$ occurs through chemical reaction with ground state Rf in reaction (r10), and through deactivation by the interaction with water in reaction (r9).

As described above, excess oxygen may be detrimental in corneal cross-linking process. As shown in FIG. 2A, when the system becomes photon-limited and oxygen-abundant, cross-links can be broken from further reactions involving superoxide, peroxide, and hydroxyl radicals. Indeed, in some cases, excess oxygen may result in net destruction of cross-links versus generation of cross-links.

As described above, a large variety of factors affect the rate of the cross-linking reaction and the amount of biomechanical stiffness achieved due to cross-linking. A number of these factors are interrelated, such that changing one factor may have an unexpected effect on another factor. However, a more comprehensive model for understanding the relationship between different factors for cross-linking treatment is provided by the photochemical kinetic reactions (r1)-(r26) identified above. Accordingly, systems and methods can adjust various parameters for cross-linking treatment according to this photochemical kinetic cross-linking model, which provides a unified description of oxygen dynamics and cross-linking activity. The model can be employed to evaluate expected outcomes based on different combinations of treatment parameters and to identify the combination of treatment parameters that provides the desired result. The parameters, for example, may include, but is not limited to: the concentration(s) and/or soak times of the applied cross-linking agent; the dose(s), wavelength (s), irradiance(s), duration(s), and/or on/off duty cycle(s) of the photoactivating light; the oxygenation conditions in the tissue; and/or presence of additional agents and solutions.

Figure 3A:
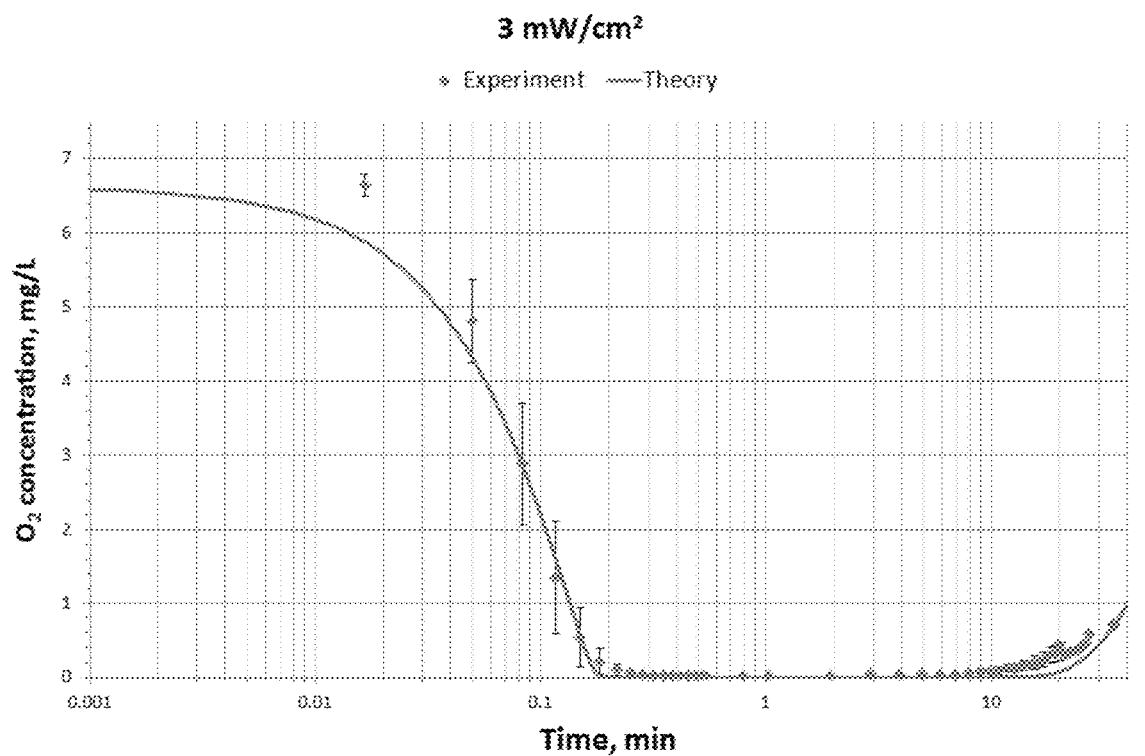
FIGS. 3A-C illustrate graphs showing the correlation between model values and experimental data for oxygen depletion experiments, where the model values are based on a model of photochemical kinetic reactions according to aspects of the present disclosure.
Figure 3B:
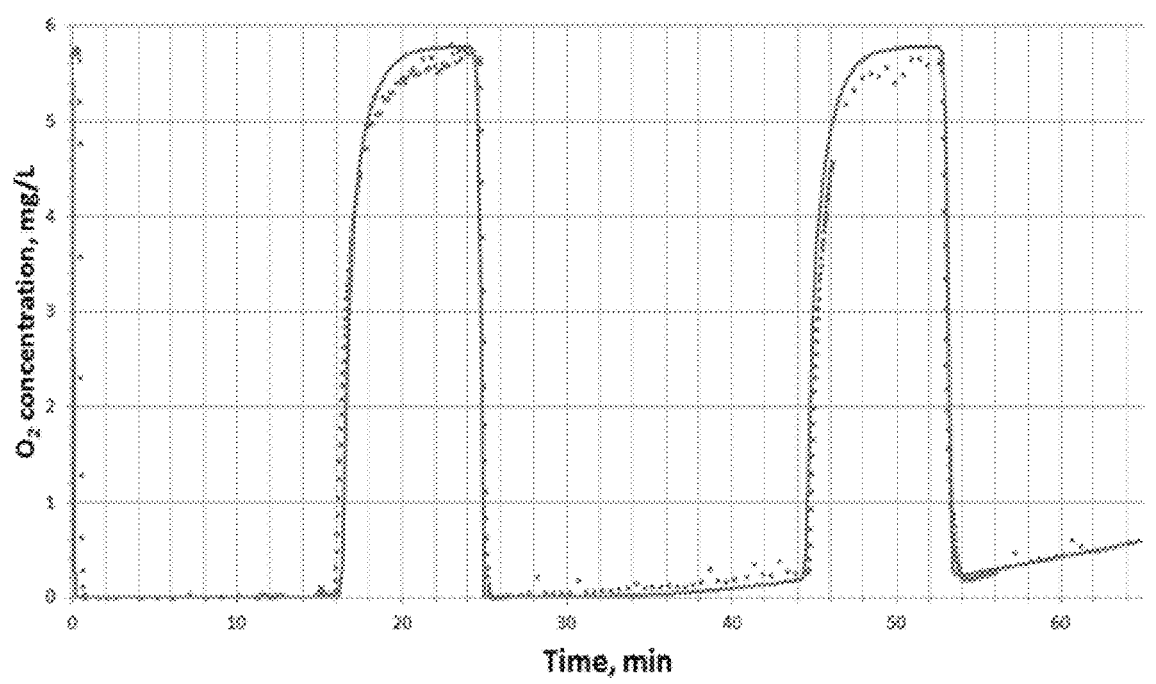
Figure 3C:
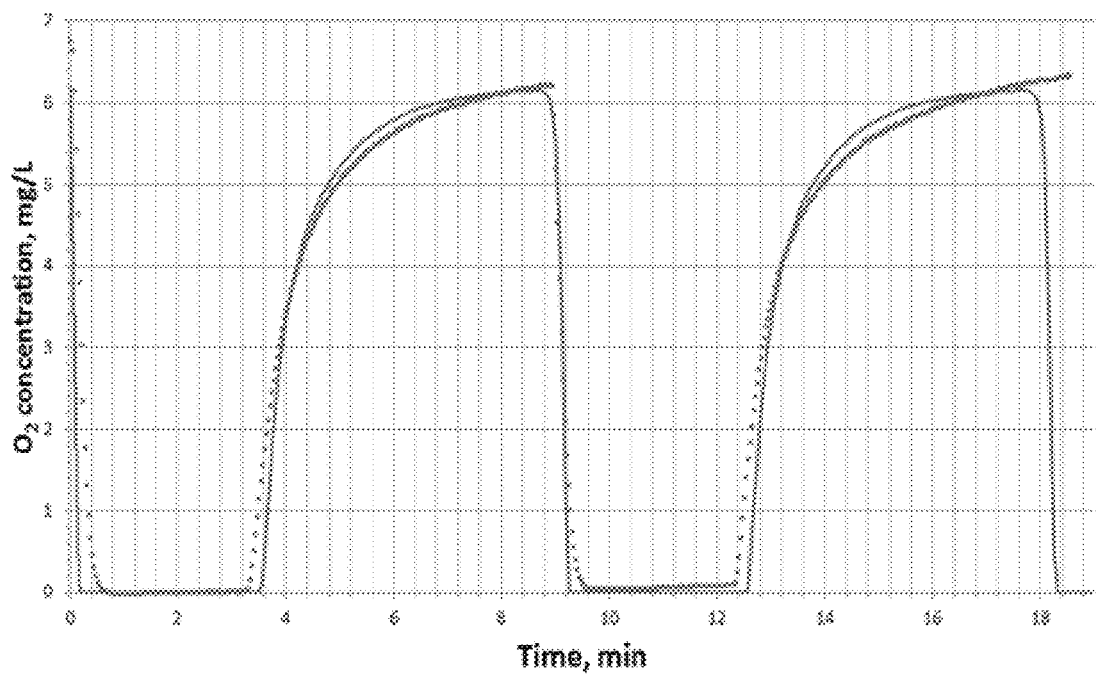

A model based on the reactions (r1)-(r19) has been validated by at least four different methods of evaluating cross-linking activity:
  Oxygen depletion experiments
  Non-linear optical microscopy fluorescence experiments
  Fluorescence data based on papain digestion method experiments
  Corneal stromal demarcation line correlation experiments For the oxygen depletion experiments, $O_2$ concentrations were measured and calculated at a depth of approximately 100 μm to approximately 200 μm for corneas treated with riboflavin. FIG. 3A illustrates a graph of data showing the correlation between the theoretical values based on the model and experimental data for corneas exposed to continuous wave UVA photoactivating light at an irradiance of 3 mW/cm². FIGS. 3B-C illustrate graphs of data showing the correlation between model values and experimental data for corneas exposed to long term pulses and short term pulses, respectively, at an irradiance of 3 mW/cm$^2$.

Figure 4:
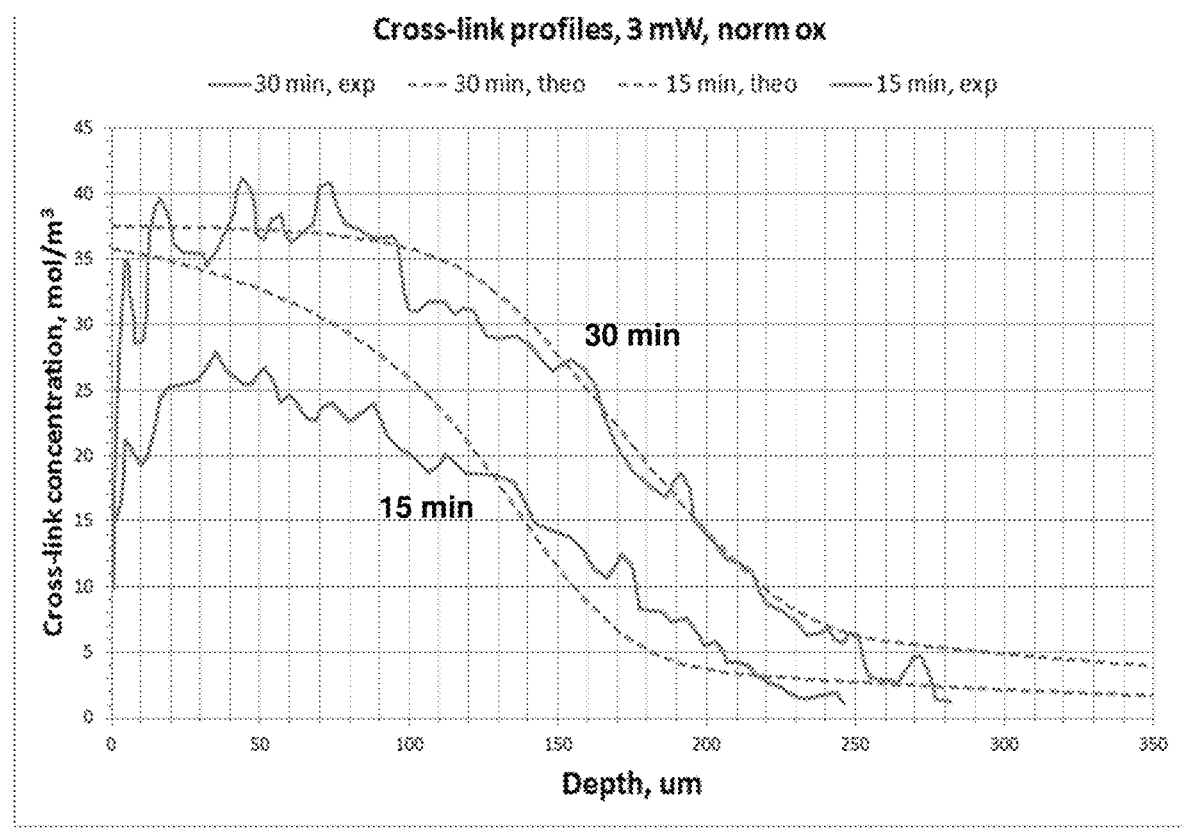
FIG. 4 illustrates a graph showing the correlation between model values and experimental data for non-linear optical microscopy fluorescence experiments, where the model values are based on a model of photochemical kinetic reactions according to aspects of the present disclosure.

For the non-linear optical microscopy fluorescence experiments, the cross-linking profiles based on corneal depth were determined for corneas treated with riboflavin and exposed to UVA photoactivating light at an irradiance of 3 mW/cm$^2$. FIG. 4 illustrates a graph of data showing the correlation between model and experimental data for corneas exposed for 15 minutes and 30 minutes. The third party experimental data was published in Dongyul Chai et al. "Quantitative Assessment of UVA-riboflavin Corneal Cross-Linking Using Nonlinear Optical Microscopy." *Investigative Ophthalmology & Visual Science*. June 2011, Vol. 52, No. 7, pp. 4231-4238, the contents of which are incorporated entirely herein by reference.

Figure 5A:
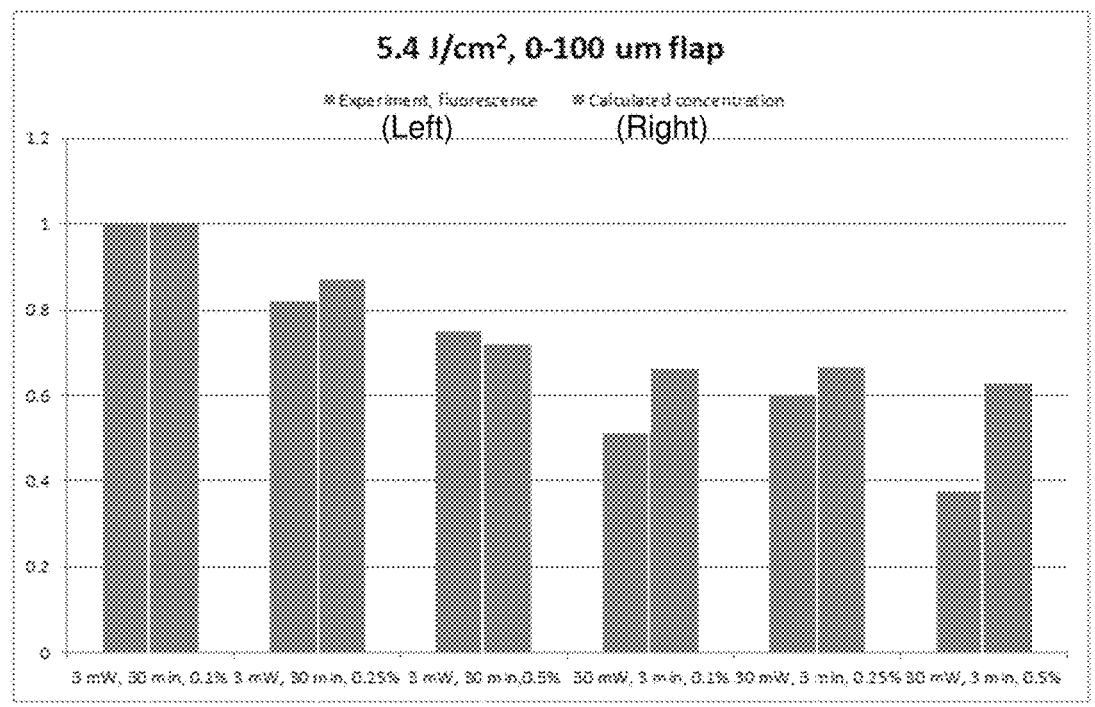
FIGS. 5A-D illustrate graphs showing the correlation between model values and experimental data for fluorescence data based on papain digestion method experiments, where the model values are based on a model of photochemical kinetic reactions according to aspects of the present disclosure.
Figure 5B:
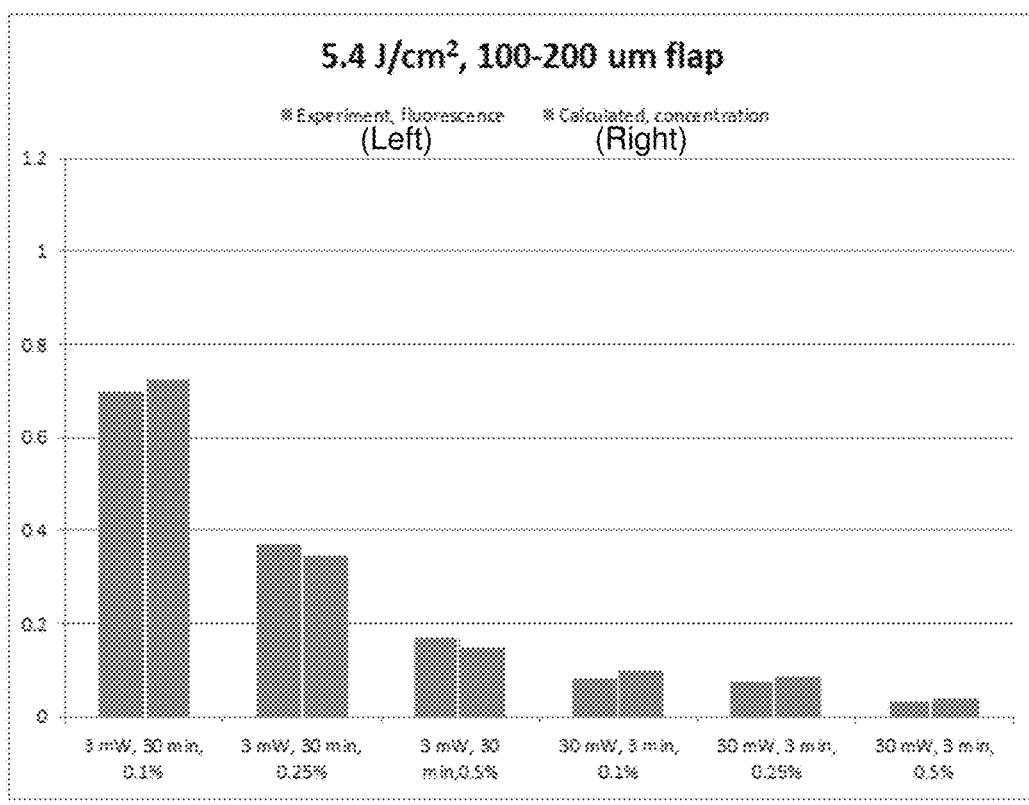
Figure 5C:
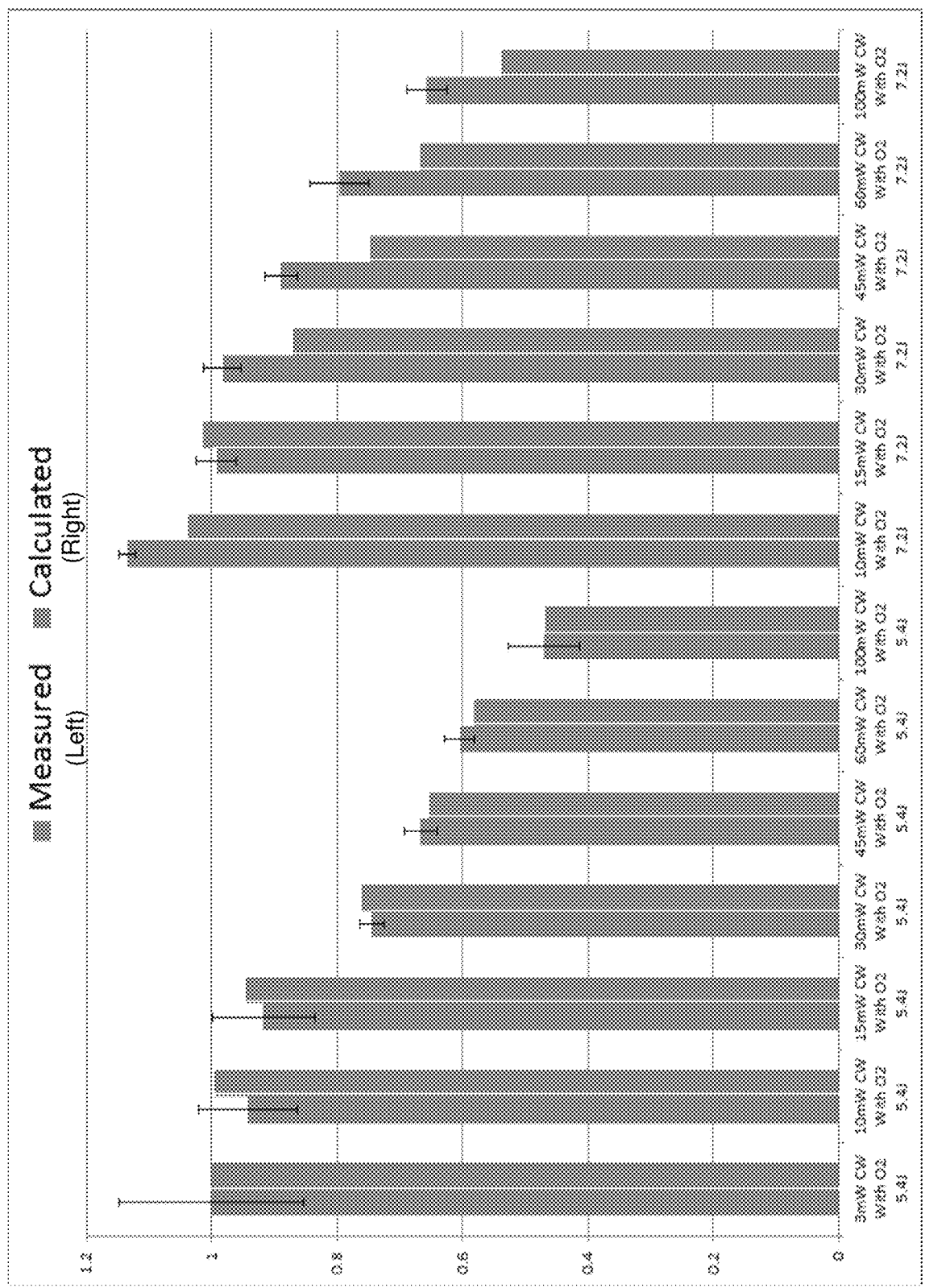
Figure 5D:
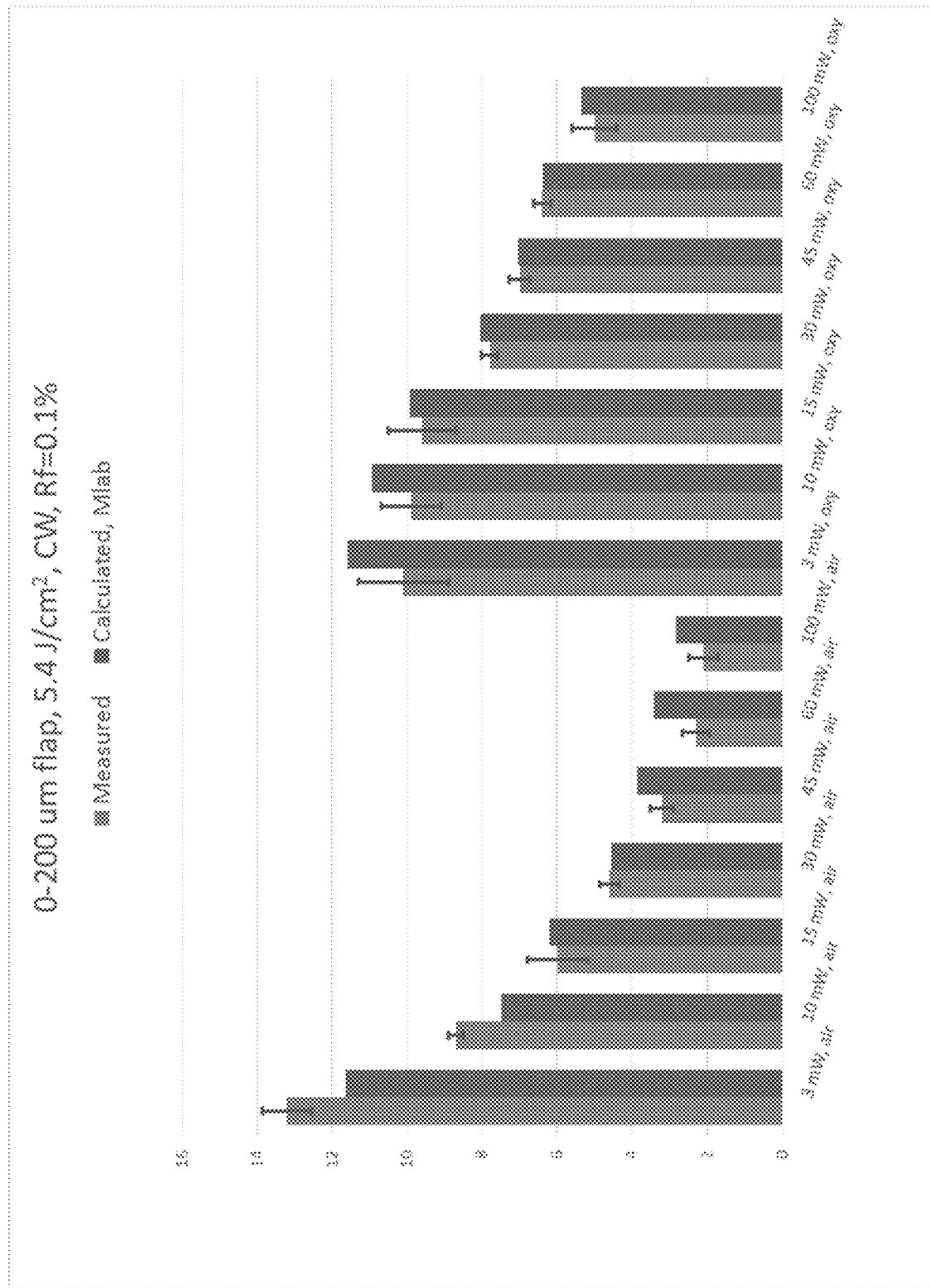

For the fluorescence data based on papain digestion method experiments, cross-linking concentrations were evaluated based on fluorescent light intensity. FIG. 5A illustrates a graph of data showing the correlation of model values and experimental data for corneal flaps (taken from 0 to approximately 100 µm deep) exposed to combinations of riboflavin concentrations (0.1%, 0.25%, and 0.5%) and 5.4 J/cm$^2$ doses of UVA photoactivating light at irradiances of 3 mW/cm$^2$ and 30 mW/cm$^2$ for 3 minutes and 30 minutes. Similarly, FIG. 5B illustrates a graph of data showing the correlation of model values and experimental data for corneal flaps (taken from approximately 100 µm to approximately 200 µm deep) exposed to combinations of riboflavin concentrations (0.1%, 0.25%, and 0.5%) and 5.4 J/cm$^2$ doses of UVA photoactivating light at irradiances of 3 mW/cm$^2$ and 30 mW/cm$^2$ for 3 minutes and 30 minutes. FIG. 5C illustrates a graph of data showing the correlation of model values and experimental data for corneal flaps treated with a concentration of riboflavin and exposed to full oxygen concentration and 5.4 J/cm$^2$ and 7.2 J/cm$^2$ doses of continuous wave UVA photoactivating light at irradiances of 3 mW/cm$^2$, 10 mW/cm$^2$, 15 mW/cm$^2$, 30 mW/cm$^2$, 45 mW/cm$^2$, 60 mW/cm$^2$, and 100 mW/cm$^2$. FIG. 5D illustrates a graph of data showing the correlation of model values and experimental data for corneal flaps (taken from approximately 0 µm to approximately 200 µm deep) treated with a concentration of 0.1% riboflavin and exposed to air or full oxygen concentration and a 5.4 J/cm$^2$ doses of continuous wave UVA photoactivating light at irradiances of 3 mW/cm$^2$, 10 mW/cm$^2$, 15 mW/cm$^2$, 30 mW/cm$^2$, 45 mW/cm$^2$, 60 mW/cm$^2$, and 100 mW/cm$^2$.

Figure 6A:
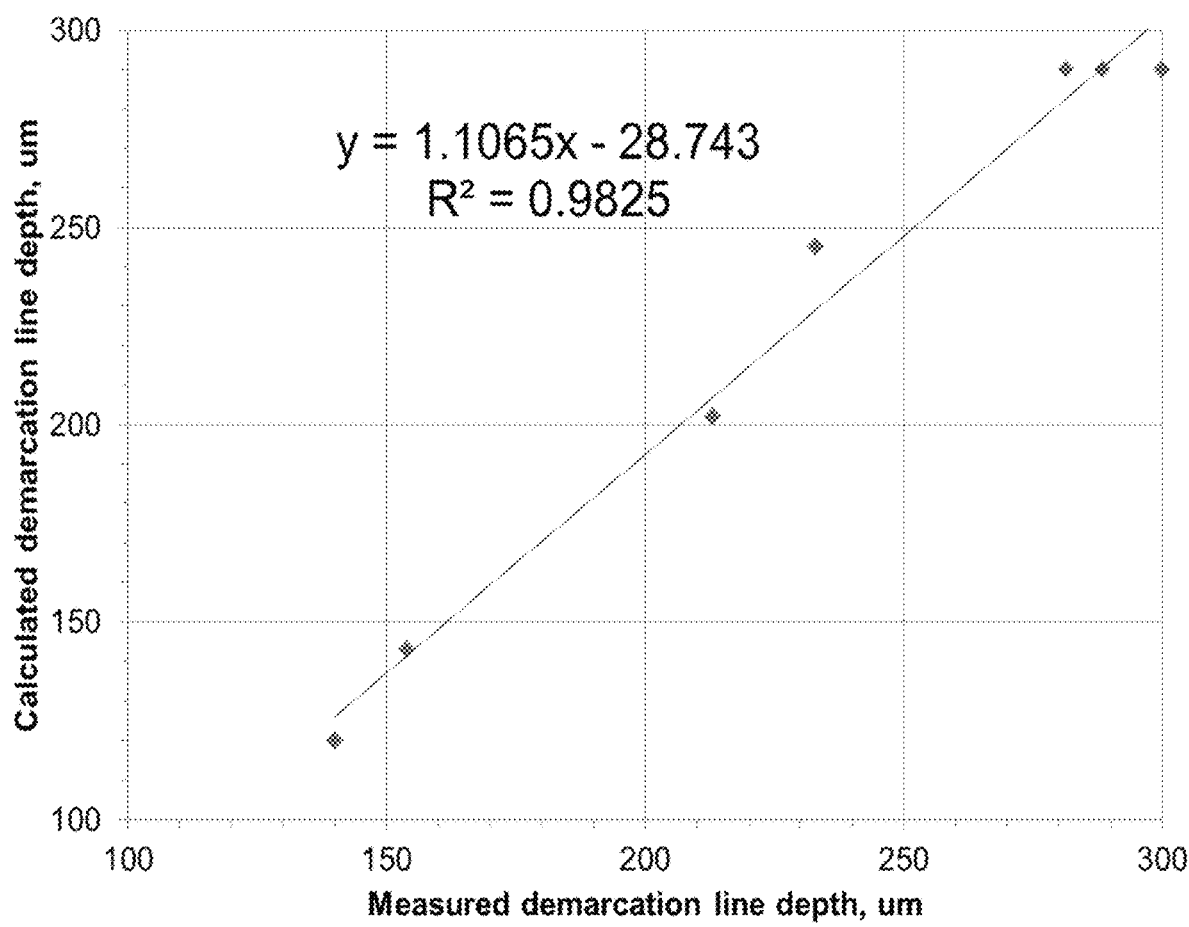

For the corneal stromal demarcation correlation experiments, corneal stromal demarcation lines were evaluated for treated corneas. Corneal stromal demarcation lines indicate the transition zone between cross-linked anterior corneal stroma and untreated posterior corneal stroma. Aspects of the method for these experiments are described further by Theo Seiler and Farhad Hafezi. "Corneal Cross-Linking-Induced Stromal Demarcation Line." *Cornea*, October 2006; 25:1057-59, the contents of which are incorporated entirely herein by reference. The corneal FIG. 6A illustrates a graph of data showing the correlation of model values and experimental data for the depths of corneal stromal demarcation lines for the protocols described in FIG. 6B.

The four evaluations described above show a strong correlation between the experimental data and the calculations generated by a model based on the photochemical kinetic reactions identified above. The model is extremely effective and accurate in predicting the results of riboflavin cross-linking treatments applied according to various combinations of parameters. Accordingly, using such a model, systems and methods can more efficiently and predictably achieve a desired profile of cross-linking activity throughout the cornea. The model allows the systems and methods to identify a more optimal combination of parameters for cross-linking treatment. Therefore, the model can be used to determine the set up for different aspects of cross-linking treatment systems as described above.

Figure 2B:
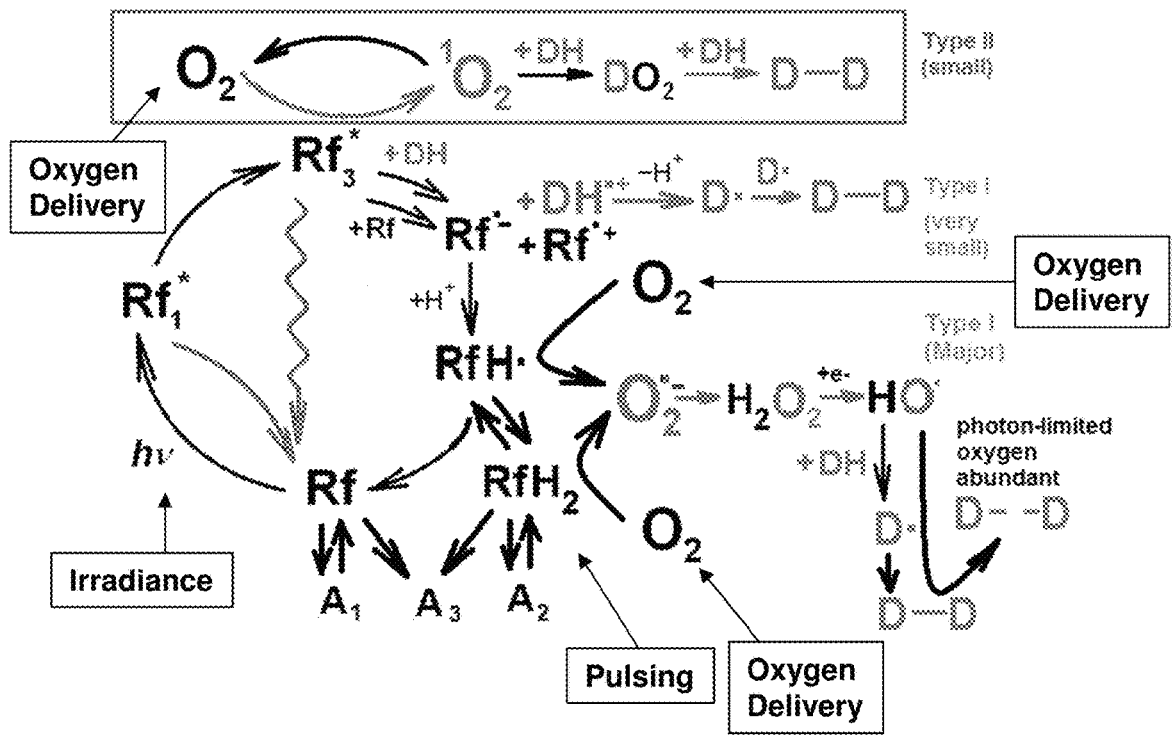

As shown in FIG. 2B, aspects of the system of reactions can be affected by different parameters. For instance, the irradiance at which photoactivating light is delivered to the system affects the photons available in the system to generate $Rf_3^*$ for subsequent reactions. Additionally, delivering greater oxygen into the system drives the oxygen-based reactions. Meanwhile, pulsing the photoactivating light affects the ability of the reduced riboflavin to return to ground state riboflavin by allowing additional time for oxygen diffusion. Of course, other parameters can be varied to control the system of reactions.

Figure 7A:
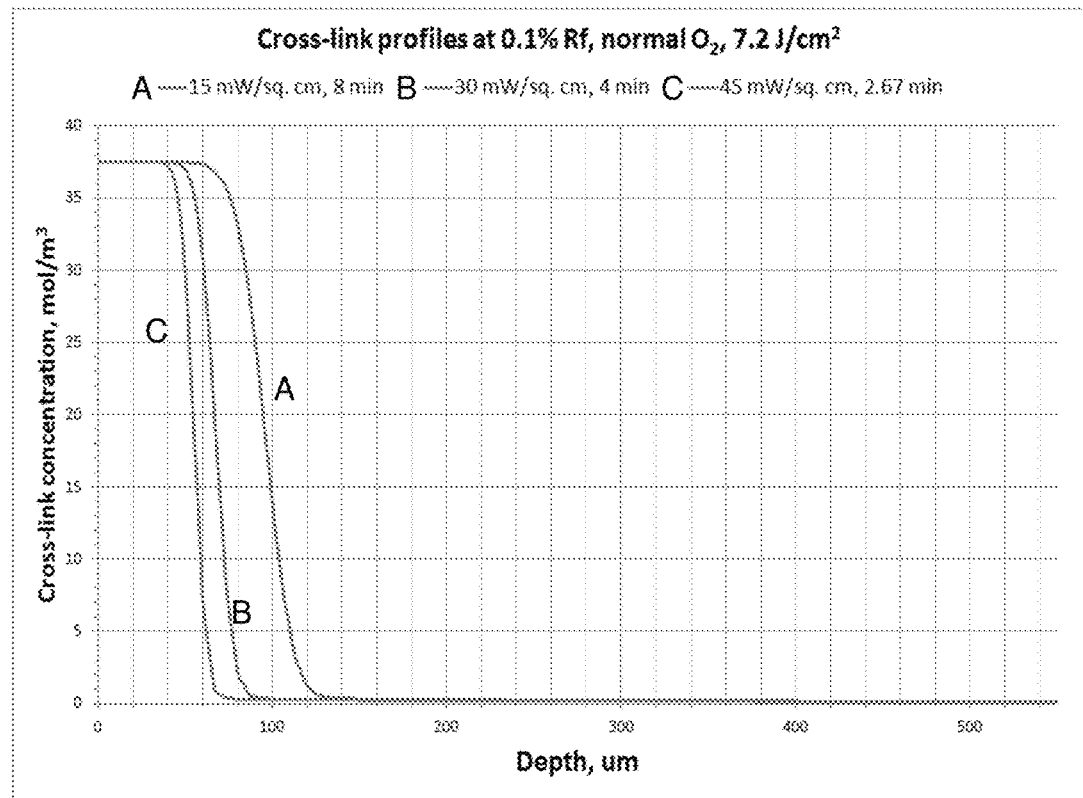
FIGS. 7A-C illustrate graphs of cross-link profiles for treatments using different protocols, as generated by a model of photochemical kinetic reactions according to aspects of the present disclosure.
Figure 7B:
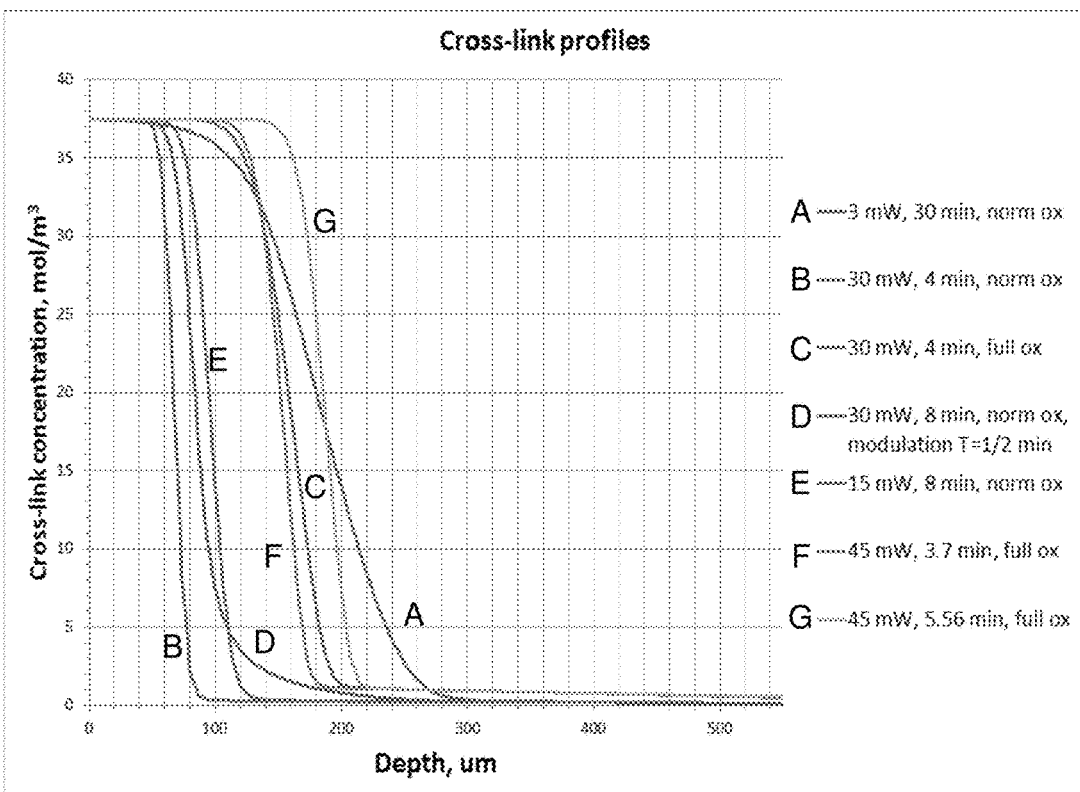
Figure 7C:
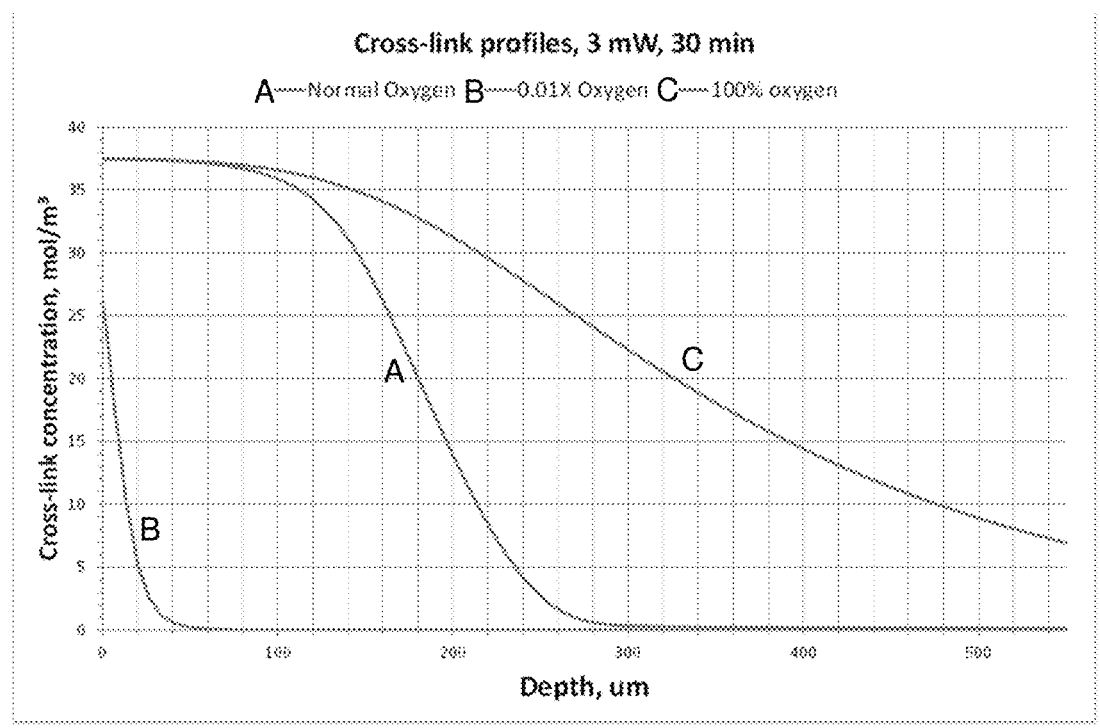

A model based on the photochemical kinetic reactions (r1)-(r26) can generate cross-link profiles for treatments using different protocols as shown in FIGS. 7A-C. In particular, each protocol determines the dose of the photoactivating UVA light, the irradiance for the UVA photoactivating light, the treatment time, and the concentration of oxygen delivered to the corneal surface. The cornea has been treated with a formulation including 0.1% concentration riboflavin. FIG. 7A illustrates cross-link profiles for treatments that deliver a dose of 7.2 J/cm$^2$ of UVA light under normal (ambient) oxygen according to different irradiances and different treatment times. FIG. 7B illustrates cross-link profiles for treatments that employ different irradiances of continuous or modulated (pulsed) UVA light and different treatment times under normal or 100% oxygen concentration. FIG. 7C illustrates cross-link profiles for treatments that deliver an irradiance of 3 mW of UVA light for 30 minutes with different oxygen conditions (normal, 100%, or 0.01×) at the corneal surface.

The cross-link profiles in FIGS. 7A-C provide the cross-link concentration as a function of corneal depth. In general, the three-dimensional distribution of cross-links in the cornea as indicated by each cross-link profile depends on the combination of different treatment parameters. Protocols employing different sets of treatment parameters can be provided as input into the model and the model can output the resulting three-dimensional distribution of cross-links in the cornea. Accordingly, the model can be used to select treatment parameters to achieve the desired distribution of cross-links in the cornea.

Figure 8A:
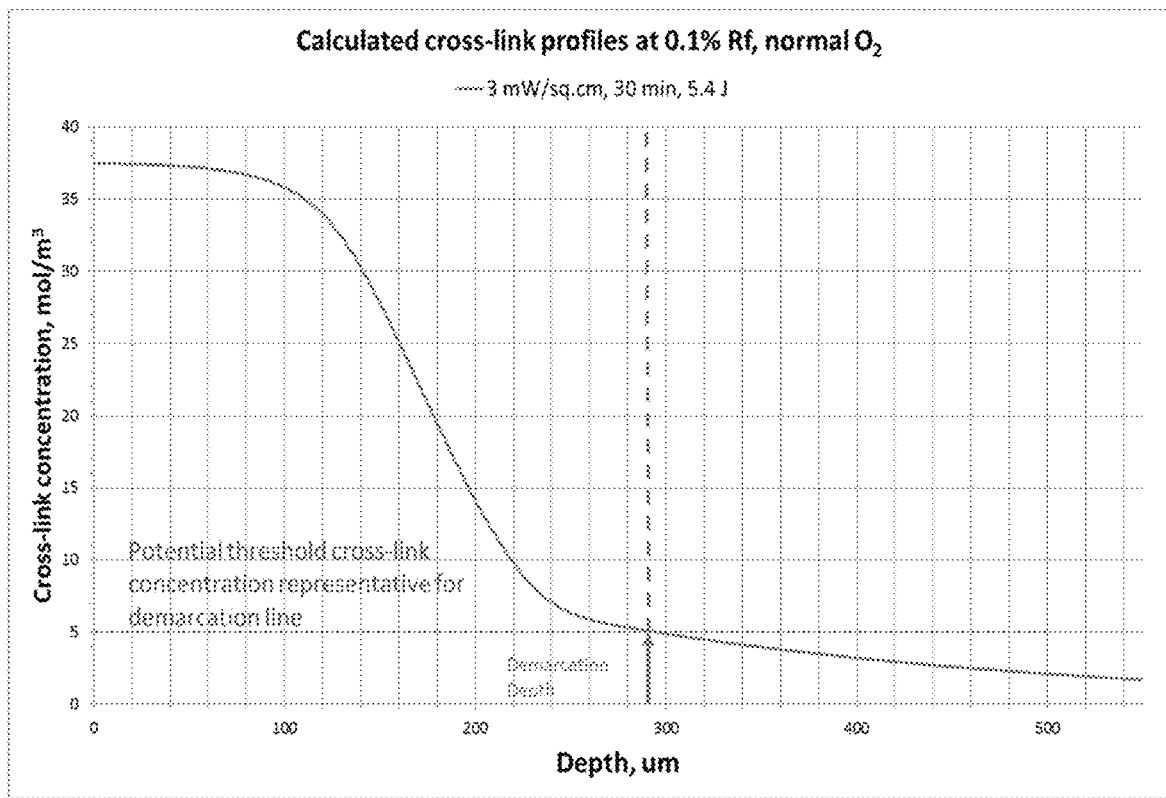
FIGS. 8A-C illustrate graphs of cross-link profiles for treatments using different protocols, as generated by a model of photochemical kinetic reactions, where the cross-link profiles are evaluated to determine the depth for a demarcation line for each protocol according to aspects of the present disclosure.
Figure 8B:
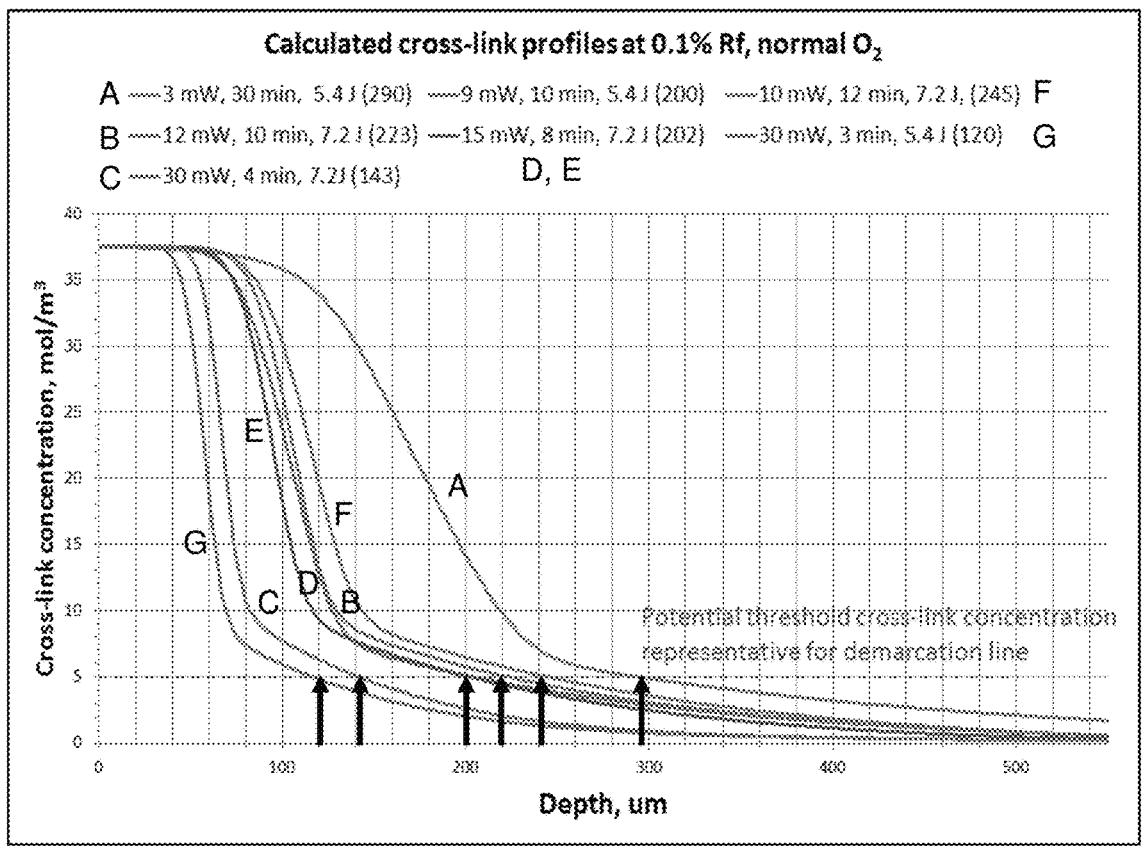
Figure 8C:
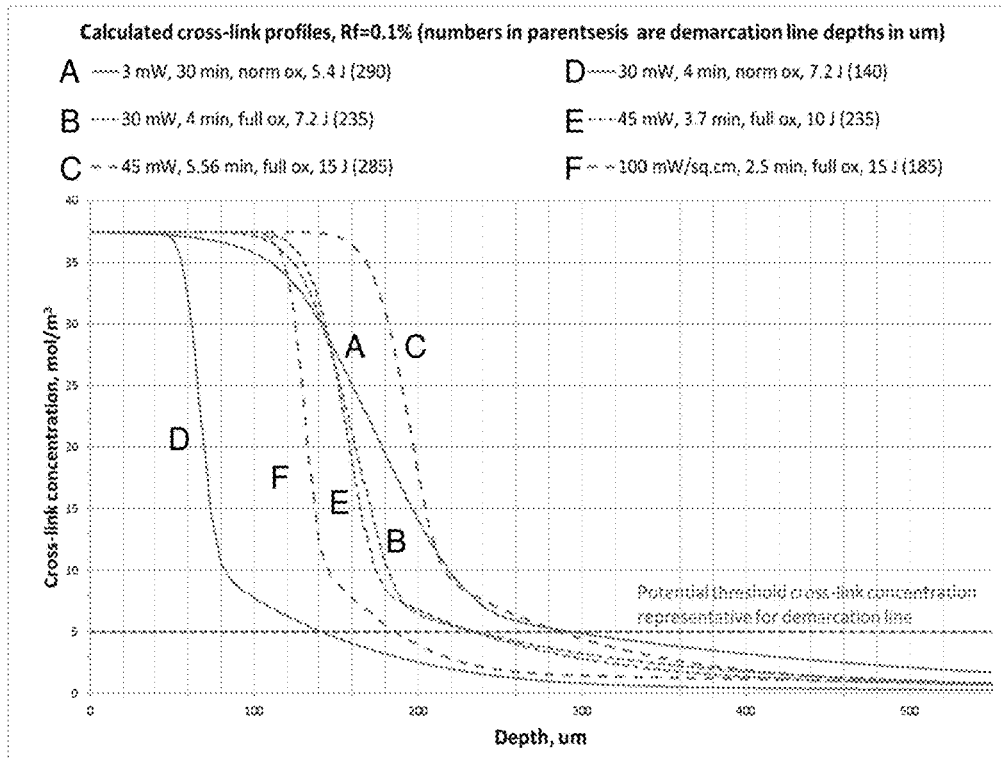

As described above, corneal stromal demarcation lines indicate the transition zone between cross-linked anterior corneal stroma and untreated posterior corneal stroma. As also shown in FIG. 8A-C, cross-link profiles generated by the model can be evaluated to determine the depth at which the demarcation line may appear at a cross-link concentration of approximately 5 mol/m$^3$. Here, the demarcation line may be understood as the threshold at which a healing response occurs in response to the distribution of cross-links as well as the effect of reactive oxygen species on the corneal tissue. The cornea has been treated with a formulation including 0.1% concentration riboflavin. FIG. 8A illustrates a cross-link profile for a treatment that delivers a dose of 5.4 J/cm$^2$ of photoactivating UVA light under normal oxygen according to an irradiance of 3 mW/cm$^2$ and a treatment time of 30 minutes. FIG. 8A shows that a cross-link concentration of approximately 5 mol/m$^3$ (demarcation line) occurs at a depth of approximately 290 µm in the resulting cross-link profile. FIG. 8B illustrates cross-link profiles for treatments that deliver different doses of photoactivating UVA light according to different irradiances and different treatment times under normal oxygen. FIG. 8C illustrates cross-link profiles for treatments that deliver different doses of photoactivating UVA light according to different irradiances and different treatment times under normal or 100% oxygen concentration.

FIGS. 8B-C shows that the depths for the demarcation line vary with the different cross-link profiles generated by the different sets of treatment parameters. The depths of the demarcation line indicated by the different cross-link profiles may be employed to select treatment parameters. For instance, treatment parameters may be selected to ensure that the cross-links do not occur at a depth where undesired damage may result to the endothelium. This analysis allows the treatment system to accommodate different corneal thicknesses, particularly thin corneas.

Figure 9A:
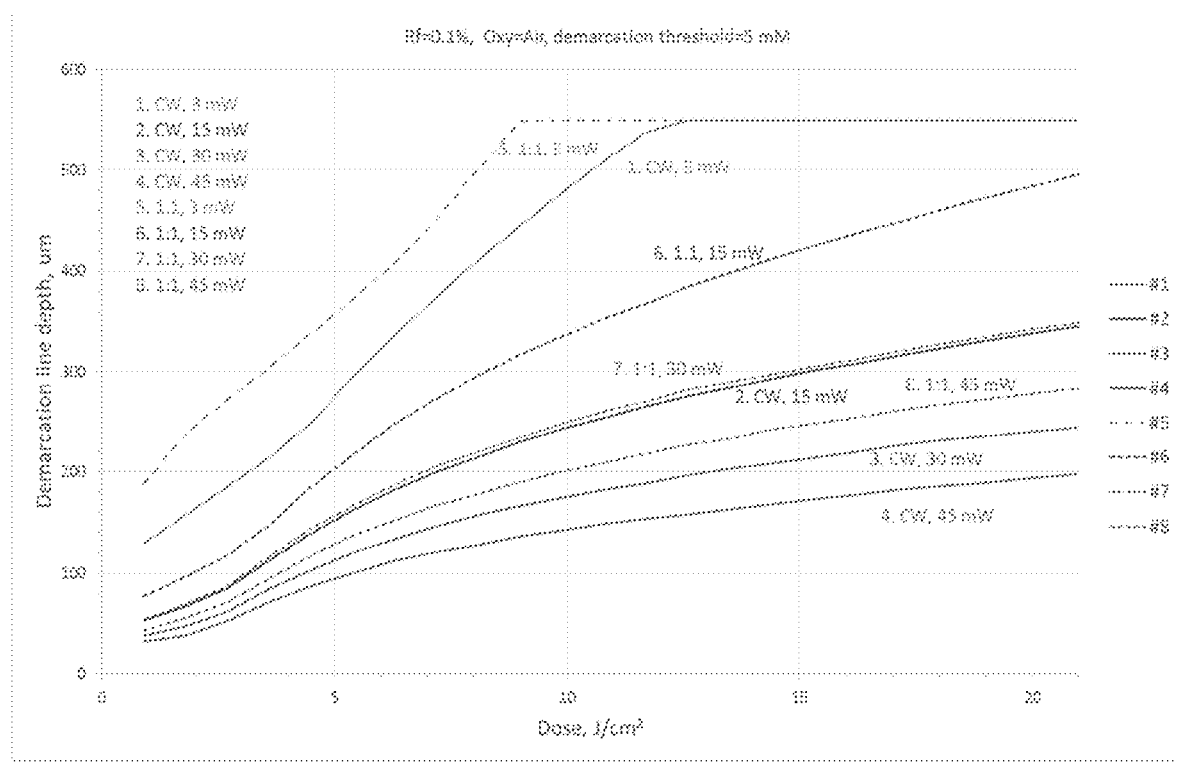
FIGS. 9A-B illustrate graphs of demarcation depth versus dose of photoactivating light based on cross-link profiles for treatments using different protocols, as generated by a model of photochemical kinetic reactions according to aspects of the present disclosure.
Figure 9B:
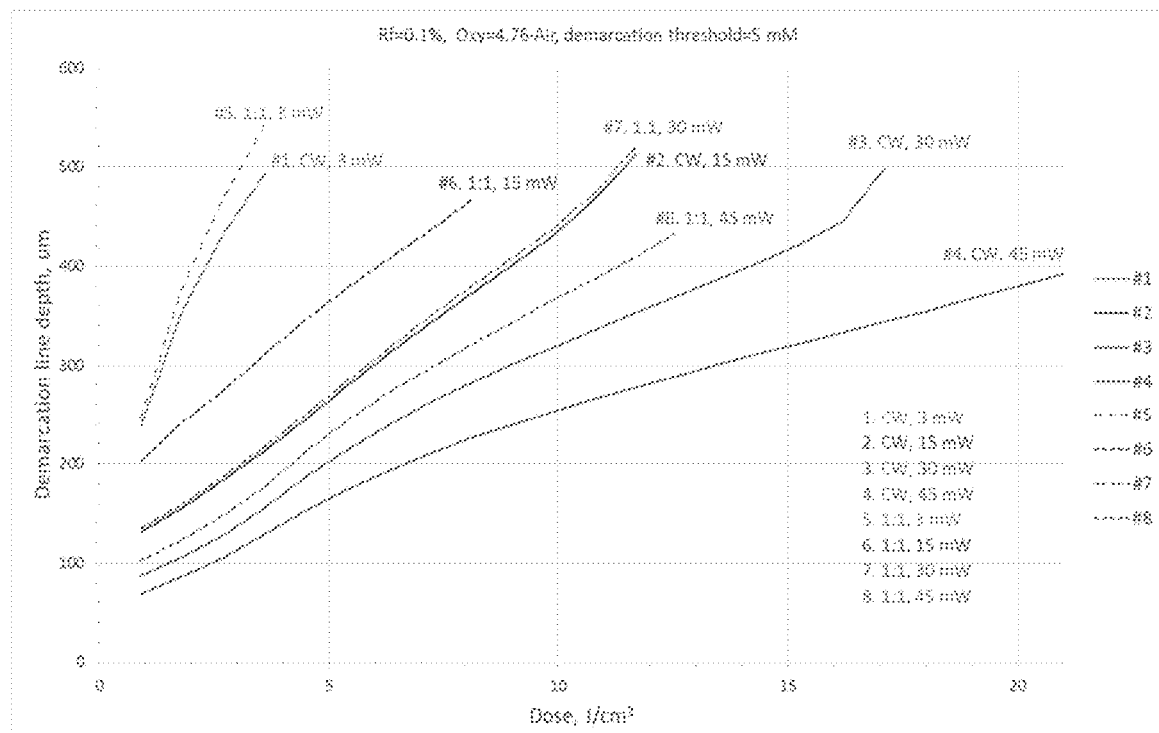

Correspondingly, FIGS. 9A-B illustrate graphs of demarcation depth (cross-link concentration of approximately 5 mol/m$^3$) as a function of dose of UVA photoactivating light. The determination of the demarcation depths are based on cross-link profiles generated by the model for treatments using different protocols. The cornea has been treated with a formulation including 0.1% concentration riboflavin. FIG. 9A illustrates graphs for treatments that deliver continuous or pulsed UVA photoactivating light according to different irradiances under normal oxygen. FIG. 9B illustrates graphs for treatments that deliver continuous or pulsed UVA photoactivating light according to different irradiances under a greater concentration of oxygen.

Figure 10:
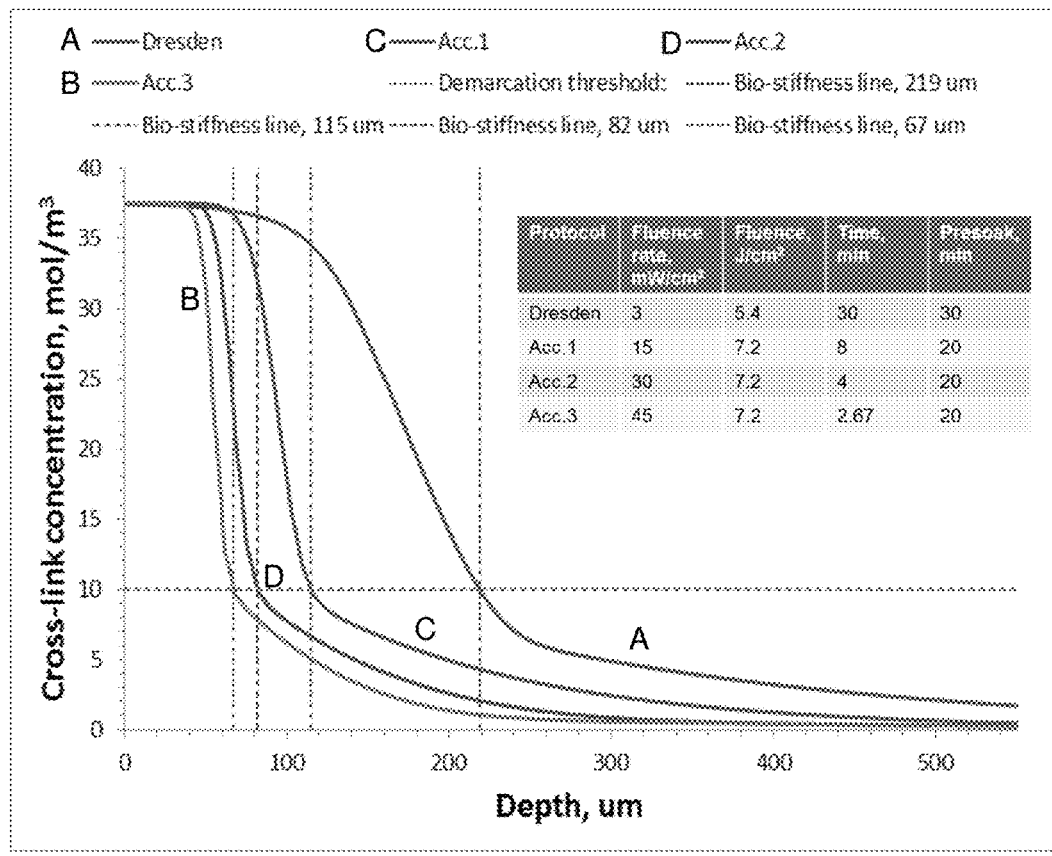
FIG. 10 illustrates a graph of cross-link profiles for treatments using different protocols as generated by a model of photochemical kinetic reactions, where the cross-link profiles are evaluated to determine the depth for a demarcation line for each protocol according to aspects of the present disclosure.
Figure 11:
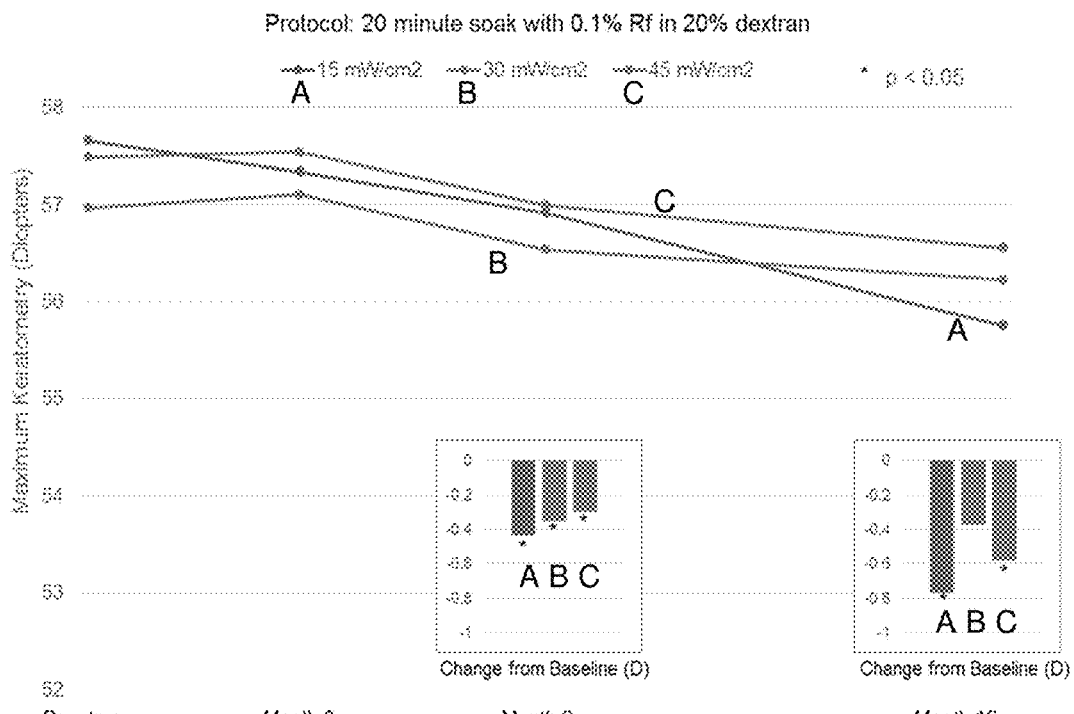
FIG. 11 illustrates the measurement of maximum keratometry ($K_{max}$) at six and twelve months relative to a baseline for corneas that were experimentally treated according to the protocols employed for FIG. 10.

FIG. 10 illustrates the cross-link profiles for treatments employing different protocols as generated by the model. FIG. 10 also shows a demarcation line that corresponds to biomechanical stiffness threshold at a cross-link concentration of 10 mol/m$^3$. The demarcation line intersects the cross-link profiles at varying depths (biomechanical stiffness depth) based on the different treatment parameters of the protocols. FIG. 11 illustrates the measurement of maximum keratometry ($K_{max}$) (diopters) at three, six, and twelve months relative to a baseline for corneas that were experimentally treated according to the protocols employed for FIG. 10.

Figure 12A:
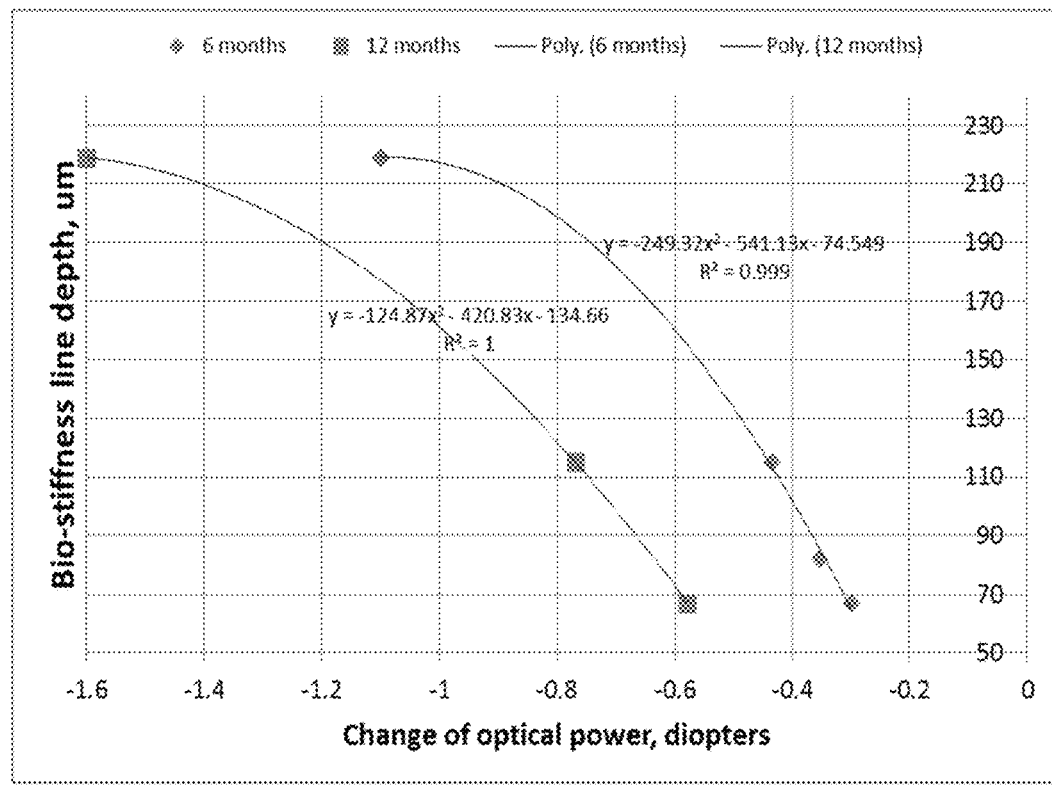
FIG. 12A illustrates a graph that plots, for the biomechanical stiffness depth determined for each protocol in FIG. 10, the experimental change of $K_{max}$ for months six and twelve corresponding to the respective protocol, according to aspects of the present disclosure.
Figure 12B:
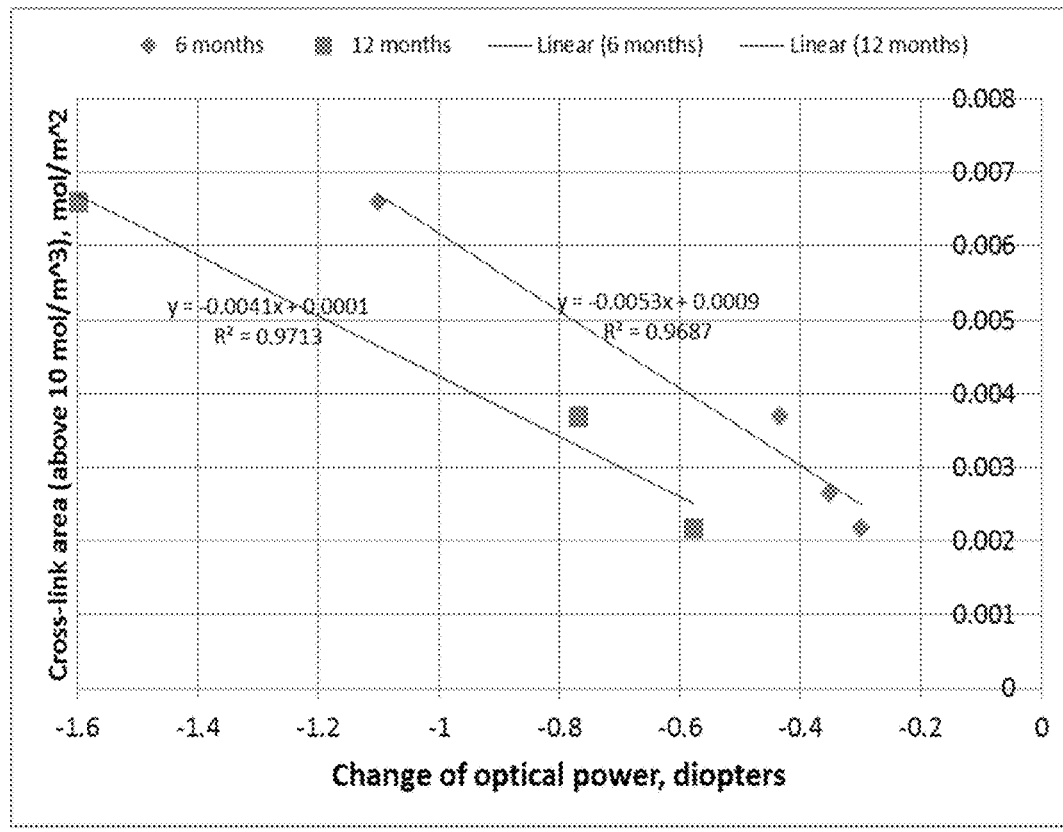
FIG. 12B illustrates a graph that plots, for the area above the demarcation line for each protocol in FIG. 10, the experimental change of $K_{max}$ for months six and twelve corresponding to the respective protocol, according to aspects of the present disclosure.

FIGS. 12A-B illustrate the correlation between the experimental data of FIG. 11 and the cross-link profiles generated for FIG. 10 by the model. For the biomechanical stiffness depth determined for each protocol in FIG. 10, FIG. 12A plots the experimental change of $K_{max}$ for months six and twelve corresponding to the respective protocol. FIG. 12A also shows a quadratic fit of the plotted data for each month six and twelve. The quadratic fit is consistent with the quadratic nature of shear forces (in the x-y plane) resulting from a force placed on a disk (along the z-axis) according to thin shell theory.

Meanwhile, for the area above the demarcation line for the cross-link profile for each protocol in FIG. 10, FIG. 12B plots the experimental change of $K_{max}$ for months six and twelve corresponding to the respective protocol. FIG. 12B also shows a linear fit of the plotted data for each month six and twelve.

The quadratic fit for the two curves in FIG. 12A are substantially similar. Similarly, the linear fit for the two curves in FIG. 12B are substantially similar. The correlations shown in FIGS. 12A-B indicate that there is a predictable biomechanical/healing response over time for a given set of treatment parameters. In view of the verification of the experimental data points, the model, as well as thin shell analysis, one can predictably determine refractive change according to the radius and depth of the disk corresponding to the myopic correction. In general, the distribution of cross-links effects refractive change. By accurately determining the distribution of cross-links, the model can be employed to determine this refractive change.

Figure 13:
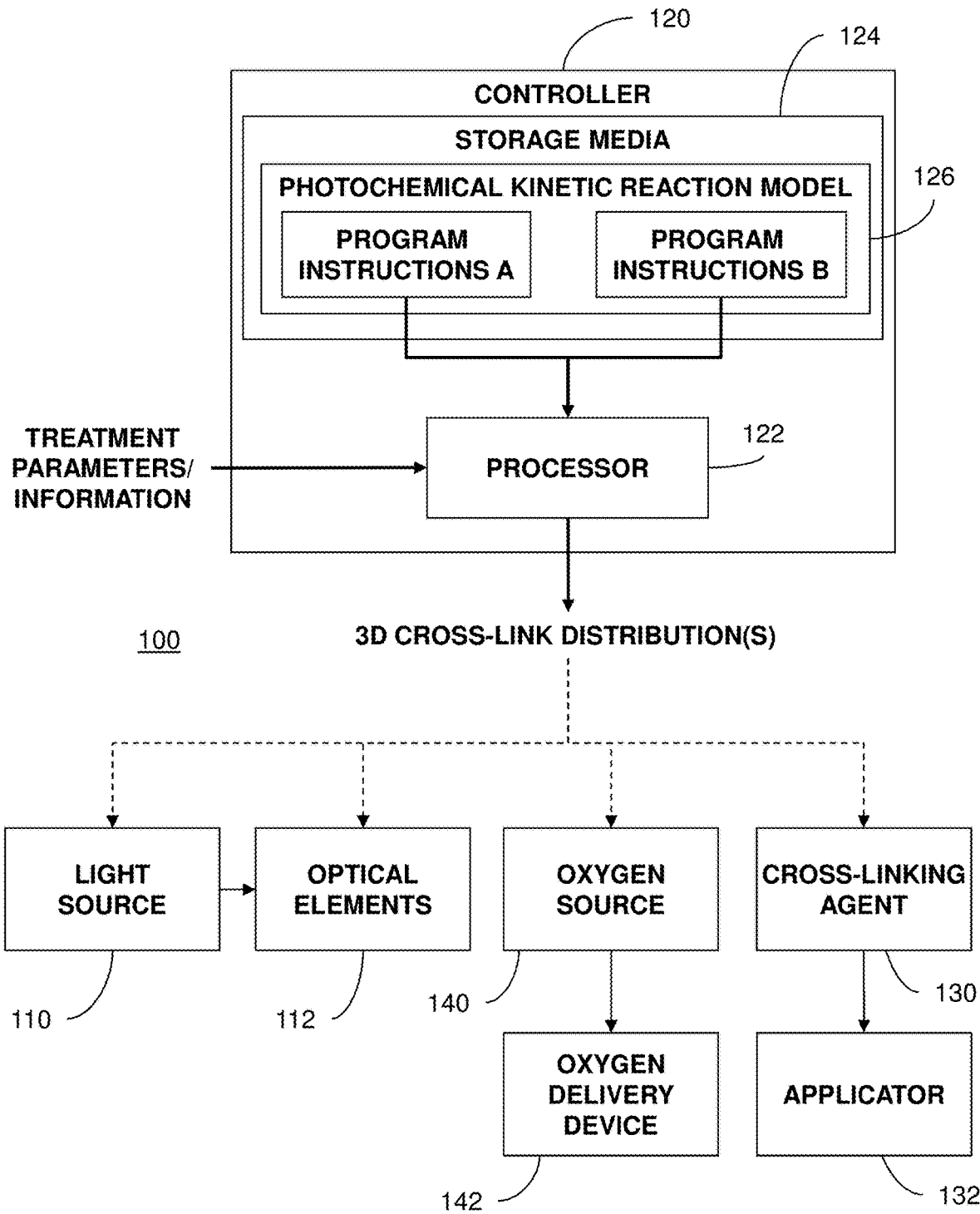
FIG. 13 illustrates an example system employing a model of photochemical kinetic reactions according to aspects of the present disclosure.

According to an embodiment, FIG. 13 illustrates the example system 100 employing a model based on the photochemical kinetic reactions (r1)-(r26) identified above to determine an amount of cross-linking that results from treatment parameters and/or other related information. The controller 120 includes a processor 122 and computer-readable storage media 124. The storage media 124 stores program instructions for determining an amount of cross-linking when the photoactivating light from the light source 110 is delivered to a selected region of a cornea treated with a cross-linking agent. In particular, a photochemical kinetic model 126 based on the reactions (r1)-(r26) may include a first set of program instructions A for determining cross-linking resulting from reactions involving reactive oxygen species (ROS) including combinations of peroxides, superoxides, hydroxyl radicals, and/or singlet oxygen and a second set of program instructions B for determining cross-linking from reactions not involving oxygen. The controller 120 receives input relating to treatment parameters and/or other related information. The controller 120 can then execute the program instructions A and B to output information relating to three-dimensional cross-link distribution(s) for the selected region of the cornea based on the input. The three-dimensional cross-link distribution(s) may then be employed to determine how to control aspects of the light source 110, the optical elements 112, the cross-linking agent 130, the applicator 132, the oxygen source 140, and/or oxygen delivery device 142 in order to achieve a desired treatment in selected region of the cornea. (Of course, the system 100 shown in FIG. 13 and this process can be used for treatment of more than one selected region of the same cornea.)

According to one implementation, the three-dimensional cross-link distribution(s) may be evaluated to calculate a threshold depth corresponding to a healing response due to the cross-links and an effect of the reactive-oxygen species in the selected region of the cornea. Additionally or alternatively, the three-dimensional cross-link distribution(s) may be evaluated to calculate a biomechanical tissue stiffness threshold depth corresponding to a biomechanical tissue response in the selected region of the cornea. The information on the depth of the healing response and/or the biomechanical tissue stiffness in the cornea can be employed to determine how to control aspects of the light source 110, the optical elements 112, the cross-linking agent 130, the applicator 132, the oxygen source 140, and/or oxygen delivery device 142. Certain healing response and/or biomechanical tissue stiffness may be desired or not desired at certain depths of the cornea.

Figure 14:
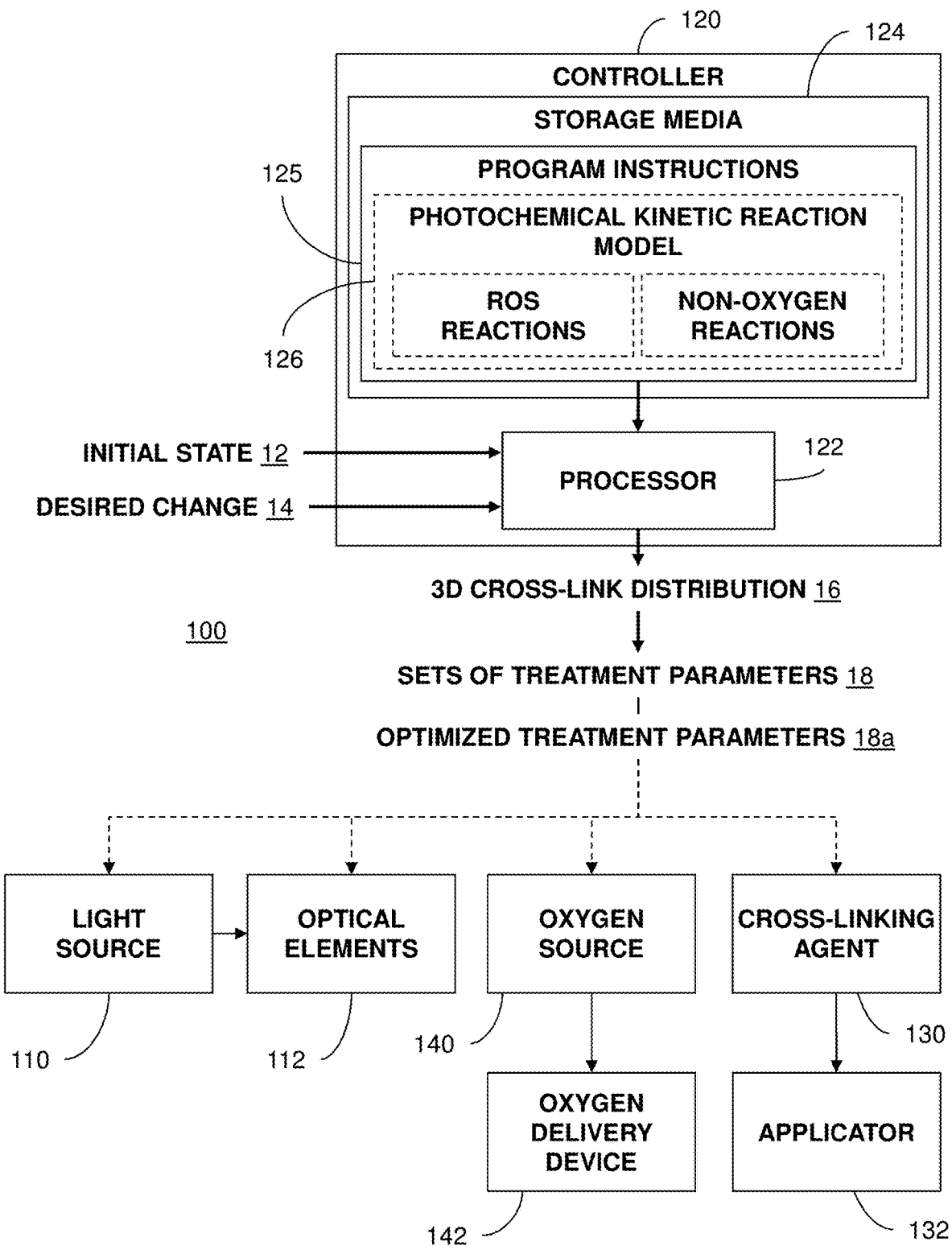
FIG. 14 illustrates an example system employing a model of photochemical kinetic reactions to provide treatment parameters for achieving desired biomechanical changes according to aspects of the present disclosure.

According to another embodiment, FIG. 14 illustrates the example system 100 employing the photochemical kinetic model 126 to determine treatment parameters for achieving desired biomechanical changes in the cornea, e.g., a refractive correction. As in FIG. 13, the controller 120 includes the processor 122 and the computer-readable storage media 124. In the example of FIG. 14, however, the storage media 124 stores program instructions 125 for determining what treatment parameters may be employed to achieve desired biomechanical changes. The program instructions 125 are based on the photochemical kinetic model 126 which employ the reactions (r1)-(r26) to determine cross-linking resulting from (i) reactions involving reactive oxygen species (ROS) including combinations of peroxides, superoxides, hydroxyl radicals, and/or singlet oxygen and (ii) reactions not involving oxygen.

Using the photochemical kinetic model 126, a three-dimensional distribution of resulting cross-links throughout the treated corneal tissue can be determined for a combination of treatment parameters. As described above, parameters for cross-linking treatment may include: the concentration(s) and/or soak times of the applied cross-linking agent; the dose(s), wavelength(s), irradiance(s), duration(s), on/off duty cycle(s), and/or other illumination parameters for the photoactivating light; the oxygenation conditions in the tissue; and/or presence of additional agents and solutions. The resulting distribution of cross-links determined from the photochemical kinetic model 126 can be correlated to a particular biomechanical change in the cornea. FIGS. 12A-B show, for instance, the correlation between the distribution of cross-links and refractive change.

As shown in FIG. 14, the controller 120 receives an input 12 relating to the initial biomechanical state of the cornea and an input 14 indicating a desired biomechanical change for the cornea, e.g., for refractive correction. The initial biomechanical state, for instance, can be determined according to approaches described in U.S. Patent Application Publication No. 2012/0215155 referenced above. In some cases, the input 12 may be provided by a measurement system communicatively coupled to the controller 120. It is understood that the initial biomechanical state may reflect the state of the cornea prior to any treatment or during a treatment.

The inputs 12, 14 may be expressed in terms of corneal topography (i.e., shape), corneal strength (i.e., stiffness), and/or corneal thickness. For instance, the desired biomechanical change for refractive correction may be determined from a correction specified (by a practitioner) in diopters, e.g., "a 1.5 diopter correction."

A desired biomechanical change in the cornea can be correlated to a particular distribution of cross-links as determined by the photochemical kinetic model 126. As such, the controller 120 can execute the program instructions 125 to determine the particular distribution of cross-links 16 that can generate the desired biomechanical change specified by the input 14 in a cornea having the initial biomechanical state specified by the input 12. After determining the distribution of cross-links 16 for the desired biomechanical change, the controller 120 can prescribe a set of treatment parameters for achieving the specified distribution of cross-links.

As the studies above establish, however, the distribution of cross-links 16 might be achieved in many cases by more than one set of treatment parameters. For instance, depending on the photochemical kinetic reactions, similar distributions of cross-links may be achieved by applying: (i) a lower dose of photoactivating light for a longer amount of time, or (ii) a higher dose of photoactivating light for a shorter amount of time. Therefore, more than one set of treatment parameters 18 for achieving the distribution of cross-links 16 may be identified.

With more than one possible set of treatment parameters 18, a practitioner can optimize the treatment for certain preferred parameters, such as treatment time or dose of photoactivating light. For instance, the practitioner may optimize the treatment parameters to achieve shorter treatment times. For this preference, the controller 120 may prescribe a set of illumination parameters that provide a larger dose of photoactivating light that yields the distribution of cross-links 16 over shorter illumination durations. Conversely, the practitioner may optimize the treatment parameters to employ smaller doses of photoactivating light. For this second preference, the controller 120 may prescribe a set of illumination parameters that provide a smaller dose of photoactivating light that yields the distribution of cross-links 16 over longer illumination durations.

In general, to achieve the distribution of cross-links 16, the controller 120 may identify any of the different combinations 18 of values for a set of treatment parameters A, B, C, D, E, etc., as described above. The practitioner can set preferences for one or more of these treatment parameters. For instance, the practitioner may initially set a preferred value or range of preferred values for parameter A. In response, the controller 120 can specify combinations of values for the remaining parameters B, C, D, E, etc., that meet the preference for parameter A while achieving the distribution of cross-links 16. The practitioner may make selections for the values of the parameters B, C, D, and/or E, etc., based on further preferences to arrive at an optimized set of treatment parameters 18a. The process of optimizing the treatment parameters may be iterative as the values for the treatment parameters are incrementally tuned to meet preferences having varying priorities.

In some embodiments, the practitioner may manage the optimization process through a series of selections and other inputs via a user interface (not shown) coupled to the controller 120. In some cases, the inputs 12, 14 may also be provided through such a user interface.

The final set of treatment parameters 18a can then be employed to determine how to control aspects of the light source 110, the optical elements 112, the cross-linking agent 130, the applicator 132, the oxygen source 140, oxygen delivery device 142, etc., in order to achieve a desired treatment in selected region of the cornea.

Figure 15:
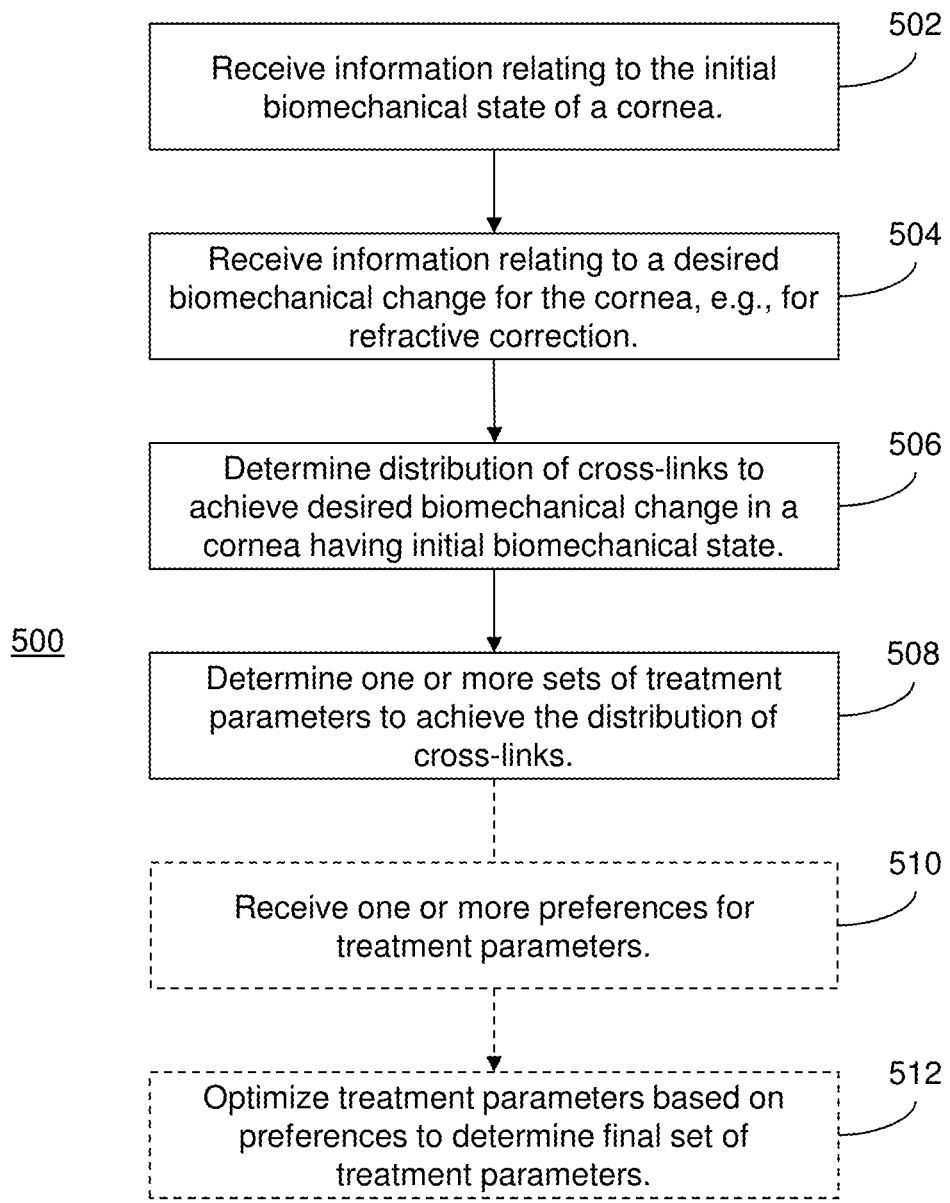
FIG. 15 an example method employing a model of photochemical kinetic reactions to determine treatment parameters for achieving desired biomechanical changes according to aspects of the present disclosure.

Correspondingly, FIG. 15 illustrates an example method 200 for employing a model of photochemical kinetic reactions (r1)-(r26) to determine treatment parameters for achieving desired biomechanical changes. In step 202, information relating to the initial biomechanical state of a cornea is received. In step 204, information relating to a desired biomechanical change for the cornea, e.g., for refractive correction, is received. In step 206, a distribution of cross-links is determined to achieve the desired biomechanical change in a cornea having the initial biomechanical state. In step 208, one or more sets of treatment parameters are determined to achieve the distribution of cross-links. In association with step 208, one or more preferences for treatment parameters may be received in step 210, and the treatment parameters may be optimized in step 212 based on the one or more preferences to determine a final set of treatment parameters that can be implemented in a treatment system (e.g., the example system 100) to achieve the distribution of cross-links.

As described above, according to some aspects of the present disclosure, some or all of the steps of the above-described and illustrated procedures can be automated or guided under the control of a controller (e.g., the controller 120). Generally, the controllers may be implemented as a combination of hardware and software elements. The hardware aspects may include combinations of operatively coupled hardware components including microprocessors, logical circuitry, communication/networking ports, digital filters, memory, or logical circuitry. The controller may be adapted to perform operations specified by a computer-executable code, which may be stored on a computer readable medium.

As described above, the controller may be a programmable processing device, such as an external conventional computer or an on-board field programmable gate array (FPGA) or digital signal processor (DSP), that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), micro-controllers, and the like, programmed according to the teachings of the example embodiments of the present disclosure, as is appreciated by those skilled in the computer and software arts. The physical processors and/or machines may be externally networked with the image capture device(s), or may be integrated to reside within the image capture device. Appropriate software can be readily prepared by programmers of ordinary skill based on the teachings of the example embodiments, as is appreciated by those skilled in the software art. In addition, the devices and subsystems of the example embodiments can be implemented by the preparation of application-specific integrated circuits or by interconnecting an appropriate network of conventional component circuits, as is appreciated by those skilled in the electrical art(s). Thus, the example embodiments are not limited to any specific combination of hardware circuitry and/or software.

Stored on any one or on a combination of computer readable media, the example embodiments of the present disclosure may include software for controlling the devices and subsystems of the example embodiments, for driving the devices and subsystems of the example embodiments, for enabling the devices and subsystems of the example embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the example embodiments of the present disclosure can be distributed for better performance, reliability, cost, and the like.

Common forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A system for corneal treatment, comprising:
   a light source configured to activate cross-linking in at least one selected region of a cornea treated with a cross-linking agent, the light source being configured to deliver photoactivating light to the at least one selected region of the cornea; and
   a controller configured to:
      receive input relating to pre-clinical patient information;
      determine a patient-specific treatment plan by analyzing the pre-clinical patient information, wherein the patient-specific treatment plan specifies a set of parameters for the light source to deliver the photoactivating light, and the set of parameters for the light source is based on a cross-linking model resulting from determined by: (A) reactions involving reactive oxygen species (ROS) including at least peroxides, superoxides, or hydroxyl radicals, and (B) reactions not involving oxygen; and
      cause the light source to be adjusted to deliver the photoactivating light according to the set of parameters.

2. The system of claim 1, further comprising an oxygen source and an oxygen delivery device configured to provide a concentration of oxygen from the oxygen source to the at least one selected region of the cornea,
   wherein the controller is further configured to receive input relating to the concentration of oxygen and to determine the set of parameters for the light source based additionally on the concentration of oxygen.

3. The system of claim 1, wherein the controller is further configured to receive input relating to the cross-linking agent and to determine the set of parameters for the light source based additionally on the cross-linking agent.

4. The system of claim 3, wherein the input relating to the cross-linking agent indicates a concentration of the cross-linking agent and a soak time for treating the cornea with the cross-linking agent.

5. The system of claim 1, wherein the set of parameters for the light source is based additionally on cross-linking resulting from reactions involving reactive oxygen species (ROS) including singlet oxygen.

6. A method for corneal treatment, comprising:
   providing a light source configured to activate cross-linking in at least one selected region of a cornea treated with a cross-linking agent, the light source being configured to deliver photoactivating light to the at least one selected region of the cornea; and
   receiving input relating to pre-clinical patient information;
   determining a patient-specific treatment plan by combining the pre-clinical patient information with finite element biomechanical computer modeling, wherein the patient-specific treatment plan specifies a set of parameters for a light source to deliver photoactivating light, and the set of parameters for the light source is based on a cross-linking model determined by: (A) reactions involving reactive oxygen species (ROS) including at least peroxides, superoxides, or hydroxyl radicals, and (B) reactions not involving oxygen; and
   causing the light source to be adjusted to deliver the photoactivating light according to the set of parameters.

7. The method of claim 6, further comprising:
providing an oxygen source and an oxygen delivery device configured to provide a concentration of oxygen from the oxygen source to the at least one selected region of the cornea;
receiving input relating to the concentration of oxygen; and
determining the set of parameters for the light source based additionally on the concentration of oxygen.

8. The method of claim 6, further comprising:
receiving input relating to the cross-linking agent; and
determining the set of parameters for the light source based additionally on the cross-linking agent.

9. The method of claim 8, wherein the input relating to the cross-linking agent indicates a concentration of the cross-linking agent and a soak time for treating the cornea with the cross-linking agent.

10. The method of claim 6, wherein the set of parameters for the light source is based additionally on cross-linking resulting from reactions involving reactive oxygen species (ROS) including singlet oxygen.

\* \* \* \* \*